US011903833B2

(12) United States Patent
Matheny

(10) Patent No.: US 11,903,833 B2
(45) Date of Patent: Feb. 20, 2024

(54) PROSTHETIC VENOUS VALVES

(71) Applicant: CorMatrix Cardiovascular, Inc., Roswell, GA (US)

(72) Inventor: Robert G Matheny, Norcross, GA (US)

(73) Assignee: Cormatrix Cardiovascular, Inc., Roswell, GA (US)

( * ) Notice: Subject to any disclaimer, the term of this patent is extended or adjusted under 35 U.S.C. 154(b) by 546 days.

(21) Appl. No.: 17/177,471

(22) Filed: Feb. 17, 2021

(65) Prior Publication Data

US 2021/0177598 A1    Jun. 17, 2021

Related U.S. Application Data

(63) Continuation-in-part of application No. 16/129,968, filed on Sep. 13, 2018, now Pat. No. 10,952,843, and
(Continued)

(51) Int. Cl.
*A61F 2/24* (2006.01)
*A61L 27/36* (2006.01)
(Continued)

(52) U.S. Cl.
CPC .......... *A61F 2/2475* (2013.01); *A61K 31/366* (2013.01); *A61K 31/40* (2013.01);
(Continued)

(58) Field of Classification Search
CPC .... A61F 2/2475; A61L 27/24; A61L 27/3625; A61L 27/54; A61L 2300/204; A61L 2300/216; A61L 2300/252; A61L 2430/20
See application file for complete search history.

(56) References Cited

U.S. PATENT DOCUMENTS 6,117,979 A    9/2000  Hendriks et al.
2009/0324674 A1  12/2009 Burne et al.
(Continued)

*Primary Examiner* — Suba Ganesan
(74) *Attorney, Agent, or Firm* — Thomas | Horstemeyer, LLP

(57) ABSTRACT

A conical shaped venous valve structure formed from collagenous mammalian tissue. The valve structure includes a plurality of fluid flow modulating means that open and allow antegrade blood to be transmitted out of the valve structure and, into and through an associated cardiovascular vessel, when the valve structure is disposed in the cardiovascular vessel and the antegrade blood exhibits a positive pressure relative to the exterior pressure, whereby a negative hydrostatic pressure gradient is generated or present proximate the flow modulating means and/or a first positive pressure differential between first internal valvular pressure and first external valvular pressure is generated proximate the flow modulating regions, and close and prevent retrograde blood from flowing into the valve structure and, thereby, cardiovascular vessel, when a positive hydrostatic pressure gradient is generated or present proximate the flow modulating means and/or the first positive pressure differential transitions to a second pressure differential between second internal valvular pressure and second external valvular pressure, the second pressure differential being lower than the first positive pressure differential.

16 Claims, 15 Drawing Sheets

Related U.S. Application Data a continuation-in-part of application No. 15/206,833, filed on Jul. 11, 2016, now Pat. No. 10,188,510, and a continuation-in-part of application No. 14/960,354, filed on Dec. 5, 2015, now Pat. No. 9,907,649, and a continuation-in-part of application No. 14/229,854, filed on Mar. 29, 2014, now Pat. No. 9,308,084.

(51) Int. Cl.
| | | |
|---|---|---|
| *A61L 27/54* | (2006.01) | |
| *A61K 31/57* | (2006.01) | |
| *A61K 31/436* | (2006.01) | |
| *A61K 38/13* | (2006.01) | |
| *A61K 31/573* | (2006.01) | |
| *A61K 31/40* | (2006.01) | |
| *A61K 31/44* | (2006.01) | |
| *A61K 31/405* | (2006.01) | |
| *A61K 31/366* | (2006.01) | |
| *A61L 27/24* | (2006.01) | |

(52) U.S. Cl.
CPC .......... *A61K 31/405* (2013.01); *A61K 31/436* (2013.01); *A61K 31/44* (2013.01); *A61K 31/57* (2013.01); *A61K 31/573* (2013.01); *A61K 38/13* (2013.01); *A61L 27/24* (2013.01); *A61L 27/54* (2013.01); *A61L 27/3625* (2013.01); *A61L 27/54* (2013.01); *A61L 2300/204* (2013.01); *A61L 2300/216* (2013.01); *A61L 2300/252* (2013.01); *A61L 2300/434* (2013.01); *A61L 2430/20* (2013.01)

(56) References Cited

U.S. PATENT DOCUMENTS

| | | |
|---|---|---|
| 2017/0014183 A1 | 1/2017 | Gifford, III et al. |
| 2018/0153686 A1 | 6/2018 | Matheny |
| 2019/0008634 A1* | 1/2019 | Matheny ............. A61L 27/3633 |
| 2020/0368178 A1 | 11/2020 | Naso et al. |

* cited by examiner

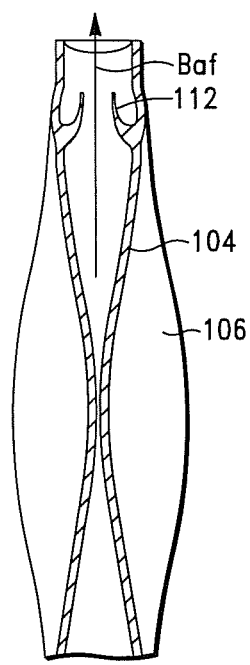
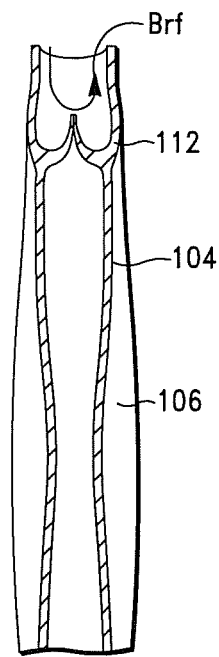
FIG. 3A            FIG. 3B
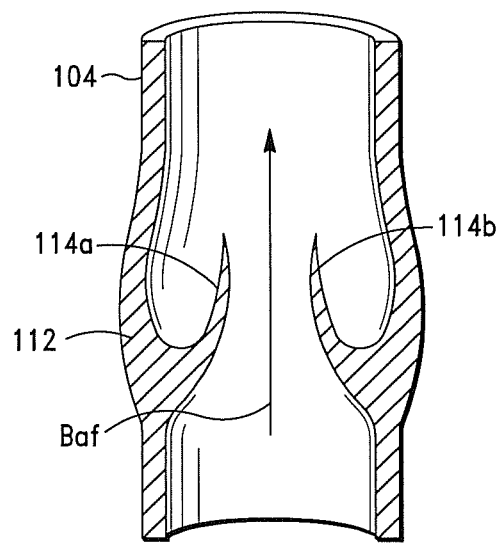
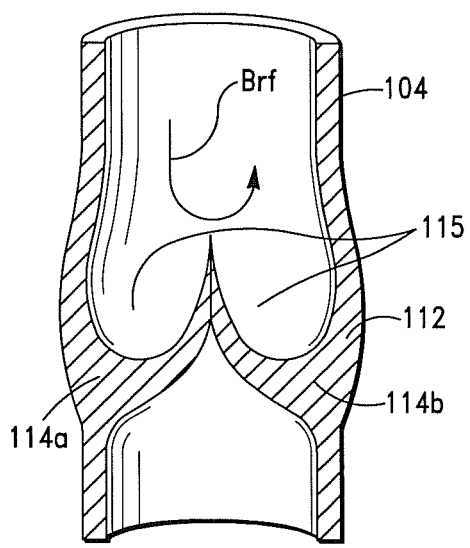
FIG. 4A            FIG. 4B

A-A

PROSTHETIC VENOUS VALVES

CROSS-REFERENCE TO RELATED APPLICATIONS

This application is a continuation-in-part of U.S. application Ser. No. 16/129,968, filed on Sep. 13, 2018, which is a continuation-in-part of U.S. application Ser. No. 15/206,833, filed on Jul. 11, 2016, now U.S. Pat. No. 10,188,510, which is a continuation-in-part application of U.S. application Ser. No. 14/960,354, filed on Dec. 5, 2015, now U.S. Pat. No. 9,907,649, which is a continuation-in-part application of U.S. application Ser. No. 14/229,854, filed on Mar. 29, 2014, now U.S. Pat. No. 9,308,084, which claims priority to U.S. Provisional Application No. 61/819,232, filed on May 3, 2013.

FIELD OF THE INVENTION

The present invention generally relates to prosthetic valves for replacing defective cardiovascular valves. More particularly, the present invention relates to improved prosthetic venous valves and methods for replacing native venous valves with same.

BACKGROUND OF THE INVENTION

As is well known in the art, the human venous system of the lower extremities, i.e., legs, includes the superficial and deep venous systems.

Referring to FIGS. 1A and 1B, the superficial venous system includes the great saphenous vein 102 and the small saphenous vein 104.

Referring now to FIGS. 2A and 2B, the deep venous system includes the external iliac 122, and anterior and posterior tibial veins 124, 126, which converge to form the small saphenous vein 104, which in turn becomes the femoral vein 130 when joined by the small saphenous vein 104.

The superficial and deep venous systems are separated from each other by connective tissue fascia and muscles and are connected by a third venous system—perforating or communicating veins.

As is also well known in the art, the superficial and deep venous systems contain a plurality of valves (referred to hereinafter as "venous valves"), which modulate blood flow through the venous systems and to the heart in conjunction with the musculoskeletal system of the lower extremities as follows:

When the skeletal muscles in the lower extremities tighten or contract during physical exertion or activity, such as illustrated by muscle 106 shown in FIG. 3A, the venous vessels in the superficial and deep venous systems are compressed, such as illustrated by the small saphenous vein 104 shown in FIG. 3A, and blood, i.e., antegrade flow thereof, exhibiting a positive antegrade fluid pressure (denoted by Arrow "$B_{af}$") is forced through the vessels of the superficial and deep venous systems, whereby the venous valves in the vessels, if functioning properly (i.e., if competent), open, such as illustrated by venous valves 112 in the small saphenous vein 104 shown in FIGS. 3A and 4A, and allow the blood ($B_{af}$) to be transmitted through the superficial and deep venous systems and to the heart.

When the skeletal muscles in the lower extremities relax, such as illustrated by muscle 106 in FIG. 3B, the venous vessels in the superficial and deep venous systems are no longer compressed, such as illustrated by the small saphenous vein 104 shown in FIG. 3B, whereby the antegrade fluid pressure is reduced and the antegrade blood is no longer forced through the vessels of the superficial and deep venous systems, whereby the venous valves in the vessels, if competent, close, such as illustrated by venous valves 112 in the small saphenous vein 104 shown in FIGS. 3B and 4B, and prevent retrograde flow of blood (denoted "$B_{rf}$") through the vessels in the superficial and deep venous systems.

Venous valves are generally bicuspid valves and, hence, comprise two (2) leaflets or cusps. If the venous valves are competent, i.e., functioning properly, antegrade blood exhibiting a positive antegrade fluid pressure ($B_{af}$) forces the free edges of the valve cusps apart to allow flow of the antegrade blood ($B_{af}$) through the associated vessel, such as illustrated by cusps 114a, 114b of venous valves 112 in the small saphenous vein 104 shown in FIGS. 3A and 4A, and to the heart.

The valve cusps of competent venous valves also form a reservoir for retrograde blood, as illustrated by cusps 114a, 114b of venous valves 112 in the small saphenous vein 104 shown in FIG. 4B (the retrograde blood reservoir denoted "115" therein), which, under pressure, forces the free edges of the valve cusps together to prevent retrograde blood flow ($B_{rf}$) through the associated vessel, such as illustrated by the small saphenous vein 104 shown in FIGS. 3B and 4B.

When the cusps of a venous valve do not close and seal properly when subjected to retrograde blood flow ($B_{rf}$), i.e., a pressure gradient across the valve, retrograde flow of blood through the associated vessel occurs and the venous valve is generally deemed incompetent.

It is well established that there are two chronic venous diseases in which incompetence of venous valves is an important factor in the pathophysiology. These are chronic venous valve insufficiency and varicose veins.

Chronic venous insufficiency is essentially caused by venous hypertension and chronic venous stasis due to valvular incompetence both of a primitive nature (or primary or essential or idiopathic) and of a secondary nature following past illnesses of the venous system(s), such as deep venous thrombosis or phlebitis.

As the vessels, i.e., veins, in the superficial and deep venous systems dilate due to increased pressure, the venous valves become less able to withstand the weight of the column of blood above them. This causes the venous vessels to dilate further and the venous valves in the vessels to fail. As the vessels fail, the effective height of the column of blood above the feet and ankles grows taller, with an increase in the pressure exerted on the tissues of the ankle and foot.

When the weight of that column of blood reaches a critical point, ulceration of tissue in the lower extremities commences. The ulcerations are very difficult to heal, since the weight of column of blood causing the ulcerations still exists and the ulcerations are typically disposed deep in the structure, often to the bone.

Chronic venous insufficiency thus typically presents in hypertension of the lower extremities, i.e., legs, in the deep, perforating and often superficial vessels, with associated pigmentation, pain, swelling and ulceration.

Varicose veins is a condition that consists of dilatation and tortuosity of the superficial vessels of the lower extremities, which typically results in cosmetic impairment, pain and ulceration. Varicose veins of the primary nature result from primary incompetence of the venous valves in the superficial venous system, which allows reflux of blood from the deep venous system to the superficial venous system.

Varicose veins of the secondary nature result from deep venous hypertension, which has damaged the venous valves in the perforating vessels, as well as the deep venous valves.

Various conventional treatments have thus been employed to treat incompetence of venous valves. The treatments generally include elevation of the lower extremities for extended periods of time and elastic support hose to compress the vessels externally.

The noted palliative treatments are, however, less than ideal and the effectiveness is quite variable. The treatments require major lifestyle changes for the patient with potentially suboptimal long term patient compliance.

Various surgical methods have also been employed to treat incompetence of venous valves. The conventional surgical methods include grafting a segment of a vessel, i.e., vein, with a competent valve from the patient's upper extremities into a lower extremity, venous transposition to bypass venous blood flow through a neighboring competent venous valve, valvuloplasty to repair diseased or defective valve cusps, and replacement of incompetent venous valves with porcine or prosthetic valves.

There are also several significant drawbacks associated with the noted conventional surgical methods. Grafting a segment of a vessel, i.e., vein, with a competent valve from a patient's upper extremity into a lower extremity is often quite complex due to the delicate nature of the veins and valves, and limited by the availability of desirable veins in the patient's upper extremities.

Valve reconstructive surgery is similarly quite complex due to the delicate nature of the veins and valves, as well as the issues often encountered when venous blood flow is impeded or totally blocked for a period of time. Valve reconstruction surgery is also often limited by irreversible damage of the valvular structure.

As indicated above, a further surgical method to treat incompetence of venous valves is to replace the incompetent venous valves with a native porcine or prosthetic valve. The prosthetic valves typically comprise synthetic, allograft and xenograft valves, which often include metal structures or components.

As discussed below, there are also several drawbacks and disadvantages associated with surgical replacement of incompetent venous valves with porcine and conventional prosthetic valves.

Native Porcine Valves

Although some native porcine valves have a geometry that is generally suitable as a replacement for diseased or defective venous valves, porcine valves are generally larger than native human venous valves, and include valve leaflets generally thicker and stiffer than the leaflets of human venous valves. The thicker valve leaflets require a greater opening pressure, which can enhance the likelihood of venous stasis and thrombus formation, when employed in the venous system.

Further, porcine valves are prone to induce undesirable immune responses in vivo due to the presence of xenogeneic antigens.

Synthetic Valves

As is well known in the art, synthetic valves, such as disclosed in U.S. Pat. No. 7,744,642, typically comprise various polymeric and metal components, which can, and in most instances will, induce an adverse inflammatory response when implanted in a patient or subject.

Many conventional synthetic valves also cause non-physiologic flow conditions and can, and often will, cause excessive dilation of the vessels with a subsequent decrease in blood flow rates.

A further disadvantage associated with such valves is that they also have a propensity to cause the formation of blood clots after implantation in a patient. Thus, recipients of such valves are typically required to take systemic anti-coagulant drugs for the rest of their lives. In addition to being expensive, these anti-coagulant drugs can themselves be dangerous in that they can cause abnormal bleeding in the recipient or patient that can lead to a hemorrhagic stroke.

In some instances, such valves also require one or more anti-proliferative agents to suppress excessive tissue ingrowth after implantation in a patient. The antiproliferative agents are typically coated on the valves and/or disposed in reservoirs and released by diffusion through a valve frame or orifice in the valve structure.

Allograft Tissue Valves

As is also well known in the art, allograft tissue valves are harvested from human sources, such as human cadavers. Unlike mechanical heart valves, allograft tissue valves typically do not promote blood clot formation and, therefore, avoid the need for prescribing an anticoagulant medication for the recipient or patient. However, there are still several drawbacks and disadvantages associated with allograft tissue valves.

A major drawback of allograft tissue valves is that such valves are typically not available in sufficient numbers to satisfy the needs of all patients who need new venous valves.

A further major drawback of allograft tissue valves is that recipients of allograft tissue valves are typically required to take systemic anti-rejection and/or immunosuppressive drugs for a predetermined period of time and, in some instances, for a lifetime. Although anti-rejection and/or immunosuppressive drugs increase the possibility that a patient will accept an allograft without complications, the drugs will often leave the recipient vulnerable to a plurality of other infectious diseases, including bacterial infections, fungal infections, viral infections and the like.

Xenograft Tissue Valves

As is additionally well known in the art, xenograft tissue valves are formed from non-human tissue sources, such as cows or pigs. Xenograft tissue valves are similarly less likely to cause blood clot formation than comparable mechanical valves. However, there are also several drawbacks and disadvantages associated with most conventional allograft tissue valves.

A major drawback associated with conventional xenograft tissue valves is that such valves often comprise glutaraldehyde processed tissue and, hence, are prone to calcification and lack the long-term durability of mechanical valves.

There thus remains a need for improved prosthetic venous valves that meet the unique blood flow requirements of the venous systems, and with minimal in vivo calcification and cytotoxicity.

It is therefore an object of the present invention to provide improved prosthetic venous valves that meet the unique blood flow requirements of the venous systems, and with minimal in vivo calcification and cytotoxicity.

It is another object of the present invention to provide improved prosthetic venous valves with optimum blood flow modulation and characteristics.

It is another object of the present invention to provide improved prosthetic venous valves that remodel, and induce remodeling of cardiovascular tissue and regeneration of new cardiovascular tissue and structures in vivo.

It is another object of the present invention to provide improved prosthetic venous valves having the capacity to deliver biologically active agents, such as growth factors, and pharmacological agents, such as anti-inflammatories, to cardiovascular tissue, when disposed proximate thereto.

It is yet another object of the present invention to provide methods for replacing diseased or defective native venous valves with improved prosthetic venous valves.

SUMMARY OF THE INVENTION

The present invention is directed to prosthetic venous valves that can be readily employed to replace incompetent, i.e., diseased or defective, native venous valves.

In a preferred embodiment of the invention, the prosthetic venous valves comprise continuous conical shaped structural members having a plurality of flow modulation means.

In some embodiments of the invention, the conical shaped structural members comprise conical shaped sheet structures.

In the noted embodiments, the flow modulation means comprise linear interstices.

In some embodiments of the invention, the conical shaped structural members comprise conical shaped ribbon structures having a plurality of elongated ribbon members.

In a preferred embodiment of the invention, the edge regions of the elongated ribbon members are positioned proximate each other and form the fluid flow modulating means.

In a preferred embodiment of the invention, the distal ends of the elongated ribbon members are in a joined relationship, wherein fluid flow through the joined distal ends of the elongated ribbon members is restricted.

In some embodiments of the invention, the prosthetic venous valves comprise an extracellular matrix (ECM) composition comprising ECM derived from a mammalian tissue source.

In some embodiments of the invention, the prosthetic venous valves comprise a polymeric composition comprising at least one polymer.

In some embodiments, the prosthetic venous valves comprise a collagenous mammalian tissue derived from a mammalian tissue source.

In some embodiments, the collagenous mammalian tissue comprises cardiac tissue.

In some embodiments of the invention, the cardiac tissue comprises pericardium tissue.

In some embodiments of the invention, the cardiac tissue comprises bovine pericardium tissue.

In some embodiments of the invention, the pericardium tissue comprises crosslinked pericardium tissue.

In some embodiments of the invention, the collagenous mammalian tissue comprises an exogenously added biologically active agent, such as a growth factor of cell.

In some embodiments of the invention, the collagenous mammalian tissue comprises a pharmacological agent (or composition), i.e., an agent or composition that is capable of producing a desired biological effect in vivo, e.g., stimulation or suppression of apoptosis, stimulation or suppression of an immune response, etc.

The present invention is also directed to replacing incompetent, i.e., diseased or defective, native venous valves with the aforedescribed prosthetic venous valves of the invention.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which:

FIG. 3A is an illustration of a venous vessel, and venous valves and skeletal muscles associated therewith, showing the skeletal muscles in a contracted configuration and antegrade blood flow through the vessel and an open venous valve resulting therefrom;

FIG. 3B is a further illustration of the venous vessel, and venous valves and skeletal muscles associated therewith shown in FIG. 3A, showing the skeletal muscles in a relaxed configuration and retrograde blood flow abated by a closed venous valve;

FIG. 4A is a further illustration of the venous vessel and a venous valve associated therewith shown in FIG. 3A, further showing antegrade blood flow through the vessel and the venous valve in an open configuration resulting therefrom;

FIG. 4B is a further illustration of the venous vessel and a venous valve associated therewith shown in FIG. 3A, further showing retrograde blood flow abated by the venous valve in a closed configuration;

FIG. 14 is a side, plan sectional view of the prosthetic venous valve shown in. FIG. 13, in accordance with the invention;

DETAILED DESCRIPTION OF THE PREFERRED EMBODIMENT

Figure 1A:
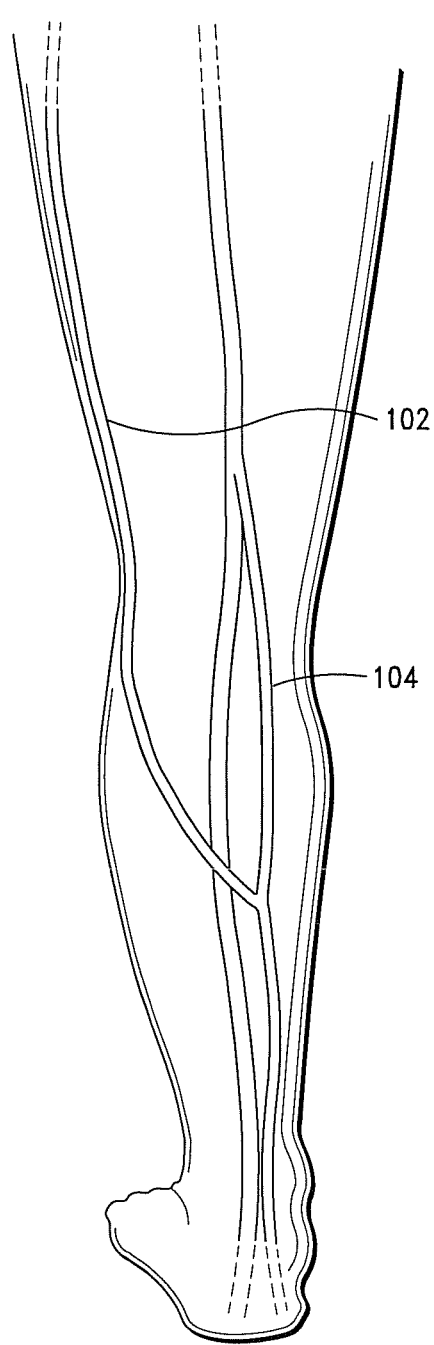
FIGS. 1A and 1B are schematic illustrations of the superficial venous system and venous vessels associated therewith.

Before describing the present invention in detail, it is to be understood that this invention is not limited to particularly exemplified apparatus, systems, structures or methods as such may, of course, vary. Thus, although a number of apparatus, systems and methods similar or equivalent to those described herein can be used in the practice of the present invention, the preferred apparatus, systems, structures and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

As used in this specification and the appended claims, the singular forms "a, "an" and "the" include plural referents unless the content clearly dictates otherwise. Thus, for example, reference to "a pharmacological agent" includes two or more such agents and the like.

Further, ranges can be expressed herein as from "about" or "approximately" one particular value, and/or to "about" or "approximately" another particular value. When such a range is expressed, another embodiment includes from the one particular value and/or to the other particular value. Similarly, when values are expressed as approximations, by use of the antecedent "about" or "approximately", it will be understood that the particular value forms another embodiment. It will be further understood that the endpoints of each of the ranges are significant both in relation to the other endpoint, and independently of the other endpoint.

It is also understood that there are a number of values disclosed herein, and that each value is also herein disclosed as "about" or "approximately" that particular value in addition to the value itself. For example, if the value "10" is disclosed, then "approximately 10" is also disclosed.

It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed.

Definitions

The terms "cardiovascular vessel" and "venous vessel" are used interchangeably herein, and mean and include any vascular structure that transports blood in and through the superficial and deep venous systems.

The term "positive hydrostatic pressure gradient", as used in connection with a prosthetic venous valve of the invention and/or a venous vessel, means the difference in pressure exerted by venous blood, i.e., antegrade and retrograde blood flow, at a given point or region of a prosthetic venous valve is in the direction of gravitational force.

The term "negative hydrostatic pressure gradient", as used in connection with a prosthetic venous valve of the invention and/or a venous vessel, means the difference in pressure exerted by venous blood, i.e., antegrade and retrograde blood flow, at a given point or region of a prosthetic venous valve is opposite to the direction of gravitational force or against gravity.

The terms "extracellular matrix", "ECM", and "ECM material" are used interchangeably herein, and mean and include a collagen-rich substance that is found in between cells in mammalian tissue, and any material processed therefrom, e.g., decellularized ECM.

The term "acellular ECM", as used herein, means ECM that has a reduced content of cells.

According to the invention, ECM can be derived from a variety of mammalian tissue sources and tissue derived therefrom, including, without limitation, small intestine submucosa (SIS), urinary bladder submucosa (UBS), stomach submucosa (SS), central nervous system tissue, epithelium of mesodermal origin, i.e., mesothelial tissue, dermal tissue, subcutaneous tissue, gastrointestinal tissue, tissue surrounding growing bone, placental tissue, omentum tissue, cardiac tissue, kidney tissue, pancreas tissue, lung tissue, and combinations thereof. The ECM can also comprise collagen from mammalian sources.

The terms "heart tissue" and "cardiac tissue" are used collectively herein, and mean and include, without limitation, mammalian tissue derived from any cardiovascular structure including, without limitation, pericardial tissue, myocardial tissue, vascular tissue and the like.

The terms "collagenous mammalian tissue" and "collagenous tissue" are used collectively herein, and mean and include, without limitation, tissue that is also derived from a mammalian tissue source.

According to the invention, the collagenous mammalian tissue can similarly be derived from a variety of mammalian tissue sources and tissue derived therefrom, including, without limitation, the heart, small intestine, large intestine, stomach, lung, liver, kidney, pancreas, peritoneum, placenta, amniotic membrane, umbilical cord, bladder, prostate, and any fetal tissue from any mammalian organ.

The collagenous mammalian tissue can also be derived from a mammalian tissue source that is devoid of xenogeneic antigens, including, without limitation, collagenous mammalian tissue that is devoid of one of the following xenogeneic antigens: galactose-alpha-1,3-galactose (also referred to as α-gal), beta-1,4 N-acetylgalactosaminyltransferase 2, membrane cofactor protein, hepatic lectin H1, cytidine monophospho-N-acetylneuraminic acid hydroxylase, swine leukocyte antigen class I and porcine endogenous retrovirus polymerase (referred to herein as "immune privileged collagenous mammalian tissue").

The term "genetically modified organism", as used herein means and includes any living organism that has at least one gene modified by artificial means, e.g., gene editing.

The term "immune privileged collagenous mammalian tissue", as used herein means and includes xenogeneic collagenous mammalian tissue that can be disposed proximate mammalian tissue with a minimal or virtually absent adverse immune response; particularly, an adverse immune response associated with xenogeneic tissue graft rejection.

According to the invention, the term "mammalian" means and includes, without limitation, warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The term "crosslinked collagenous mammalian tissue", as used herein, means and includes mammalian tissue that exhibits at least 25% chemical bonding of adjacent chains of molecules, i.e., collagen fibrils, which comprise the collagenous mammalian tissue.

The term "polymer", as used herein means and includes, without limitation, polyurethane urea, porous polyurethane urea (Artelon®), polypropylene, poly(ε-caprolactone) (PCL), poly(glycerol sebacate) (PGS), polytetrafluoroethylene (PTFE), poly(styrene-block-isobutylene-block-Styrene) (SIBS), polyglycolide (PGA), polylactide (PLA), polydioxanone (a polyether-ester), polylactide-co-glycolide, polyamide esters, polyalkalene esters, polyvinyl esters, polyvinyl alcohol, polyanhydrides, polyurethanes, polydimethylsiloxanes, poly(ethylene glycol), polytetrafluoroethylene (Teflon™) and polyethylene terephthalate (Dacron™).

The term "natural polymer", as used herein means and includes, without limitation, polysaccharides (e.g., starch and cellulose), proteins (e.g., gelatin, casein, silk, wool, etc.), and polyesters (e.g., polyhydroxyalkanoates).

The term "biologically active agent", as used herein, means and includes an agent that induces or modulates a physiological or biological process, or cellular activity, e.g., induces proliferation, and/or growth and/or regeneration of tissue.

The term "biologically active agent" thus means and includes a growth factor, including, without limitation, fibroblast growth factor-2 (FGF-2), transforming growth factor beta (TGF-β) and vascular endothelial growth factor (VEGF).

The term "biologically active agent" also means and includes a cell, including, without limitation, human embryonic stem cells, myofibroblasts, mesenchymal stem cells, and hematopoietic stem cells.

The term "biologically active agent" also means and includes an exosome and/or microsome.

The terms "exosome" and "microsome" as used herein mean and include a lipid bilayer structure that contains or encapsulates a biologically active agent and/or pharmacological agent, including, without limitation, a growth factor, e.g., TGF-β, TGF-α, VEGF and insulin-like growth factor (IGF-I), a cytokine, e.g., interleukin-10 (IL-10), a transcription factor and microRNA (miRNA).

The term "biologically active agent" also means and includes agents commonly referred to as a "protein", "peptide" and "polypeptide", including, without limitation, collagen (types I-V), proteoglycans and glycosaminoglycans (GAGs).

The terms "pharmacological agent", "active agent" and "drug" are used interchangeably herein, and mean and include an agent, drug, compound, composition of matter or mixture thereof, including its formulation, which provides some therapeutic, often beneficial, effect. This includes any physiologically or pharmacologically active substance that produces a localized or systemic effect or effects in animals, including warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The terms "pharmacological agent", "active agent" and "drug" thus mean and include, without limitation, antibiotics, anti-arrhythmic agents, anti-viral agents, analgesics, steroidal anti-inflammatories, non-steroidal anti-inflammatories, anti-neoplastics, anti-spasmodics, modulators of cell-extracellular matrix interactions, proteins, hormones, growth factors, matrix metalloproteinases (MMPs), enzymes and enzyme inhibitors, anticoagulants and/or anti-thrombotic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

The terms "pharmacological agent", "active agent" and "drug" also mean and include, without limitation, atropine, tropicamide, dexamethasone, dexamethasone phosphate, betamethasone, betamethasone phosphate, prednisolone, triamcinolone, triamcinolone acetonide, fluocinolone acetonide, anecortave acetate, budesonide, cyclosporine, FK-506, rapamycin, ruboxistaurin, midostaurin, flurbiprofen, suprofen, ketoprofen, diclofenac, ketorolac, nepafenac, lidocaine, neomycin, polymyxin b, bacitracin, gramicidin, gentamicin, oyxtetracycline, ciprofloxacin, ofloxacin, tobramycin, amikacin, vancomycin, cefazolin, ticarcillin, chloramphenicol, miconazole, itraconazole, trifluridine, vidarabine, ganciclovir, acyclovir, cidofovir, ara-amp, foscarnet, idoxuridine, adefovir dipivoxil, methotrexate, carboplatin, phenylephrine, epinephrine, dipivefrin, timolol, 6-hydroxydopamine, betaxolol, pilocarpine, carbachol, physostigmine, demecarium, dorzolamide, brinzolamide, latanoprost, sodium hyaluronate, insulin, verteporfin, pegaptanib, ranibizumab, and other antibodies, antineoplastics, anti-VEGFs, ciliary neurotrophic factor, brain-derived neurotrophic factor, bFGF, Caspase-1 inhibitors, Caspase-3 inhibitors, α-Adrenoceptors agonists, NMDA antagonists, Glial cell line-derived neurotrophic factors (GDNF), pigment epithelium-derived factor (PEDF), NT-3, NT-4, NGF and IGF-2.

The terms "pharmacological agent", "active agent" and "drug" also mean and include the Class I-Class V antiarrhythmic agents disclosed in Applicant's U.S. Pat. Nos. 9,119,841, 10,188,509, 10,188,510 and 10,143,778, and Co-pending application Ser. Nos. 16/129,968 and 16/990,236, including, without limitation, (Class Ia) quinidine, procainamide and disopyramide; (Class Ib) lidocaine, phenytoin and mexiletine; (Class Ic) flecainide, propafenone and moricizine; (Class II) propranolol, esmolol, timolol, metoprolol and atenolol; (Class III) amiodarone, sotalol, ibutilide and dofetilide; (Class IV) verapamil and diltiazem) and (Class V) adenosine and digoxin.

The terms "pharmacological agent", "active agent" and "drug" also mean and include, without limitation, the antibiotics disclosed in Applicant's U.S. Pat. Nos. 9,119,841, 10,188,509, 10,188,510 and 10,143,778, and Co-pending application Ser. Nos. 16/129,968 and 16/990,236, including, without limitation, aminoglycosides, cephalosporins, chloramphenicol, clindamycin, erythromycins, fluoroquinolones, macrolides, azolides, metronidazole, penicillin, tetracyclines, trimethoprim-sulfamethoxazole, gentamicin and vancomycin.

As indicated above, the terms "pharmacological agent", "active agent" and "drug" also mean and include an anti-inflammatory.

The terms "anti-inflammatory" and "anti-inflammatory agent" are also used interchangeably herein, and mean and include a "pharmacological agent" and/or "active agent formulation", which, when a therapeutically effective amount is administered to a subject, prevents or treats bodily tissue inflammation i.e., the protective tissue response to injury or destruction of tissues, which serves to destroy, dilute, or wall off both the injurious agent and the injured tissues.

The terms "anti-inflammatory" and "anti-inflammatory agent" thus include the anti-inflammatories disclosed in Applicant's U.S. Pat. Nos. 9,119,841, 10,188,509, 10,188,510 and 10,143,778, and Co-pending application Ser. Nos. 16/129,968 and 16/990,236, including, without limitation, desoximetasone, dexamethasone dipropionate, cloticasone propionate, diftalone, fluorometholone acetate, fluquazone, meseclazone, mesterolone, methandrostenolone, methenolone, methenolone acetate, methylprednisolone suleptanate, halopredone acetate, alclometasone dipropionate, apazone, balsalazide disodium, cintazone cormethasone acetate, cortodoxone, diflorasone diacetate, diflumidone sodium, endrysone, fenpipalone, flazalone, fluretofen, fluticasone propionate, isoflupredone acetate, nabumetone, nandrolone, nimazone, oxyphenbutazone, oxymetholone, phenbutazone, pirfenidone, prifelone, proquazone, rimexolone, seclazone, tebufelone and testosterone.

The terms "pharmacological agent", "active agent" and "drug" also mean and include the statins, i.e., HMG-CoA reductase inhibitors, disclosed in Applicant's U.S. Pat. Nos. 9,119,841, 10,188,509, 10,188,510 and 10,143,778, and Co-pending application Ser. Nos. 16/129,968 and 16/990,236, including, without limitation, atorvastatin, cerivastatin, fluvastatin and lovastatin.

The terms "pharmacological agent", "active agent", "drug" and "active agent formulation" further mean and include the anti-proliferative agents disclosed in Applicant's U.S. Pat. Nos. 9,119,841, 10,188,509, 10,188,510 and 10,143,778, and Co-pending application Ser. Nos. 16/129, 968 and 16/990,236, including, without limitation, paclitaxel, sirolimus and derivatives thereof, including everolimus.

The term "pharmacological composition", as used herein, means and includes a composition comprising a "pharmacological agent" and/or any additional agent or component identified herein.

Additional biologically active and pharmacological agents are set forth in priority U.S. application Ser. No. 15/206,833, now U.S. Pat. No. 10,188,510, which is expressly incorporated herein in its entirety.

The term "therapeutically effective", as used herein, means that the amount of the "pharmacological agent" and/or "biologically active agent" and/or "pharmacological composition" and/or "biologically active composition" administered is of sufficient quantity to ameliorate one or more causes, symptoms, or sequelae of a disease or disorder. Such amelioration only requires a reduction or alteration, not necessarily elimination, of the cause, symptom, or sequelae of a disease or disorder.

The terms "patient" and "subject" are used interchangeably herein, and mean and include warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The term "comprise" and variations of the term, such as "comprising" and "comprises," means "including, but not limited to" and is not intended to exclude, for example, other additives, components, integers or steps.

The term "comprise" and variations of the term, such as "comprising" and "comprises," as used in connection with the a prosthetic valve composition and/or mammalian tissue, also means a composition and/or mammalian tissue employed to form a prosthetic valve structure, such as a sheet member, and, hence, a prosthetic valve of the invention.

The following disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

As stated above, the present invention is directed to improved prosthetic valves and methods for replacing incompetent, i.e., diseased or defective, native venous valves with same.

Although the prosthetic valves are described in connection with prosthetic venous valves and the replacement of native venous valves therewith, it is to be understood that the prosthetic valves of the invention are not limited to prosthetic venous valves and the replacement of native venous valves therewith. Indeed, according to the invention, the prosthetic valves of the invention can also be readily employed to replace other cardiovascular valves, including heart valves.

As indicated above, native venous valves include a plurality of leaflets or cusps, which, if competent, open when subjected to antegrade blood flow ($B_{af}$), such as cusps 114a, 114b of venous valves 112 shown in FIGS. 4A and 4B, and allow the antegrade blood therethrough and into and through an associated venous vessel, such as the small saphenous vein 104 shown in FIG. 4A, and close to prevent backflow or retrograde blood flow ($B_{rf}$) through the valves, and, thereby, the associated vessel, as illustrated in FIG. 4B.

Figure 5A:
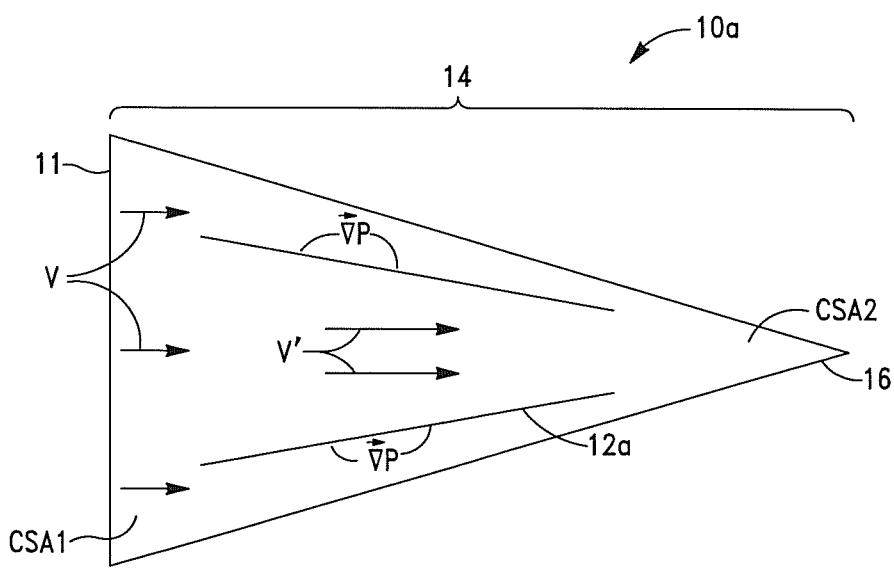
FIG. 5A is a schematic illustration of a prosthetic "sheet structure" venous valve, in accordance with the invention.
Figure 5B:
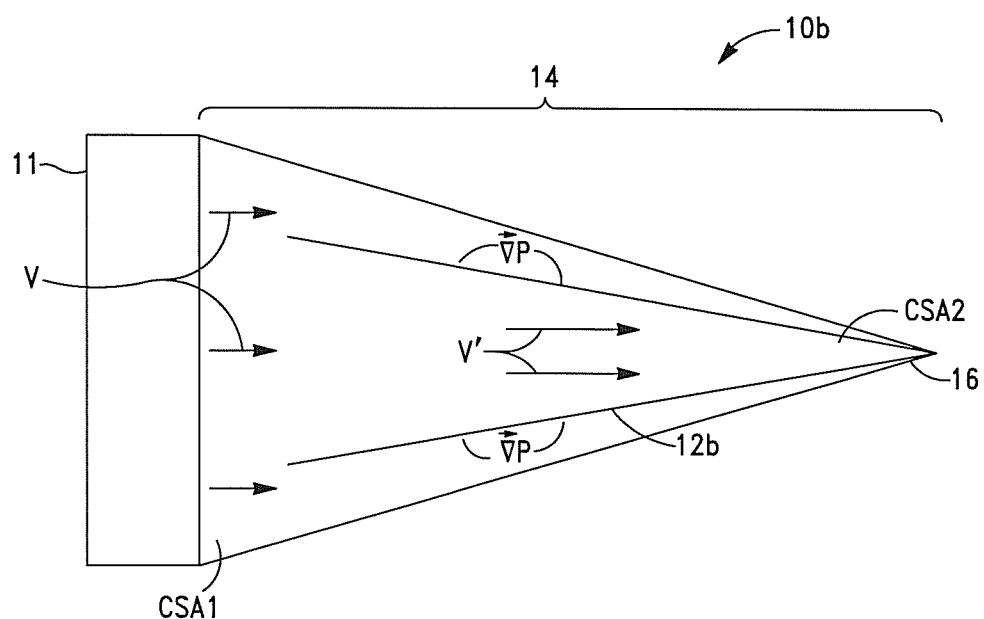
FIG. 5B is a schematic illustration of a prosthetic "ribbon structure" venous valve, in accordance with the invention.

Referring now to FIGS. 5A and 5B, there are shown schematic illustrations of the prosthetic venous valves of the invention. As illustrated in FIGS. 5A and 5B and indicated above, in a preferred embodiment of the invention, the prosthetic venous valves comprise continuous conical shaped structural members having a plurality of flow modulation means.

As illustrated in FIG. 5A, in some embodiments of the invention, the prosthetic venous valves comprise conical shaped "sheet structures" (denoted "10a"), such as the conical shaped valves disclosed in Applicant's U.S. Pat. Nos. 10,188,509, 10,188,510 and 10,188,513, and U.S. application Ser. Nos. 16/440,504 and 16/553,499, which are incorporated by reference herein in their entirety.

In the noted conical shaped sheet structure embodiments, the flow modulation means (denoted generally "12a") comprise linear interstices.

As illustrated in FIG. 5B, in some embodiments of the invention, the conical shaped structural members comprise conical shaped "ribbon structures" (denoted "10b").

In a preferred embodiment of the invention, the edge regions of the elongated ribbon members are positioned proximate each other and form the fluid flow modulating means (denoted generally "12b").

In a preferred embodiment of the invention, the distal ends of the elongated ribbon members are in a joined relationship, wherein fluid flow through the joined distal ends of the elongated ribbon members is restricted.

In some embodiments of the invention, the proximal ends of the prosthetic venous valves of the invention comprise an annular ring that is designed and configured to securely engage the prosthetic venous valves to a venous vessel wall (and, hence, cardiovascular tissue associated therewith).

In some embodiments of the invention, the annular ring comprises at least one anchoring mechanism that is configured to position the prosthetic venous valves proximate a vessel luminal wall and maintain contact therewith for a pre-determined anchor support time period.

According to the invention, the anchoring mechanisms can comprise various forms and materials, such as the anchoring mechanisms disclosed in U.S. Pat. Nos. 9,044,319 and 8,808,363, which are incorporated by reference herein in their entirety.

According to the invention, the prosthetic venous valves and/or annular rings and/or structural rings of the invention can comprise various biocompatible materials and compositions formed therefrom.

Figures 15, 16:
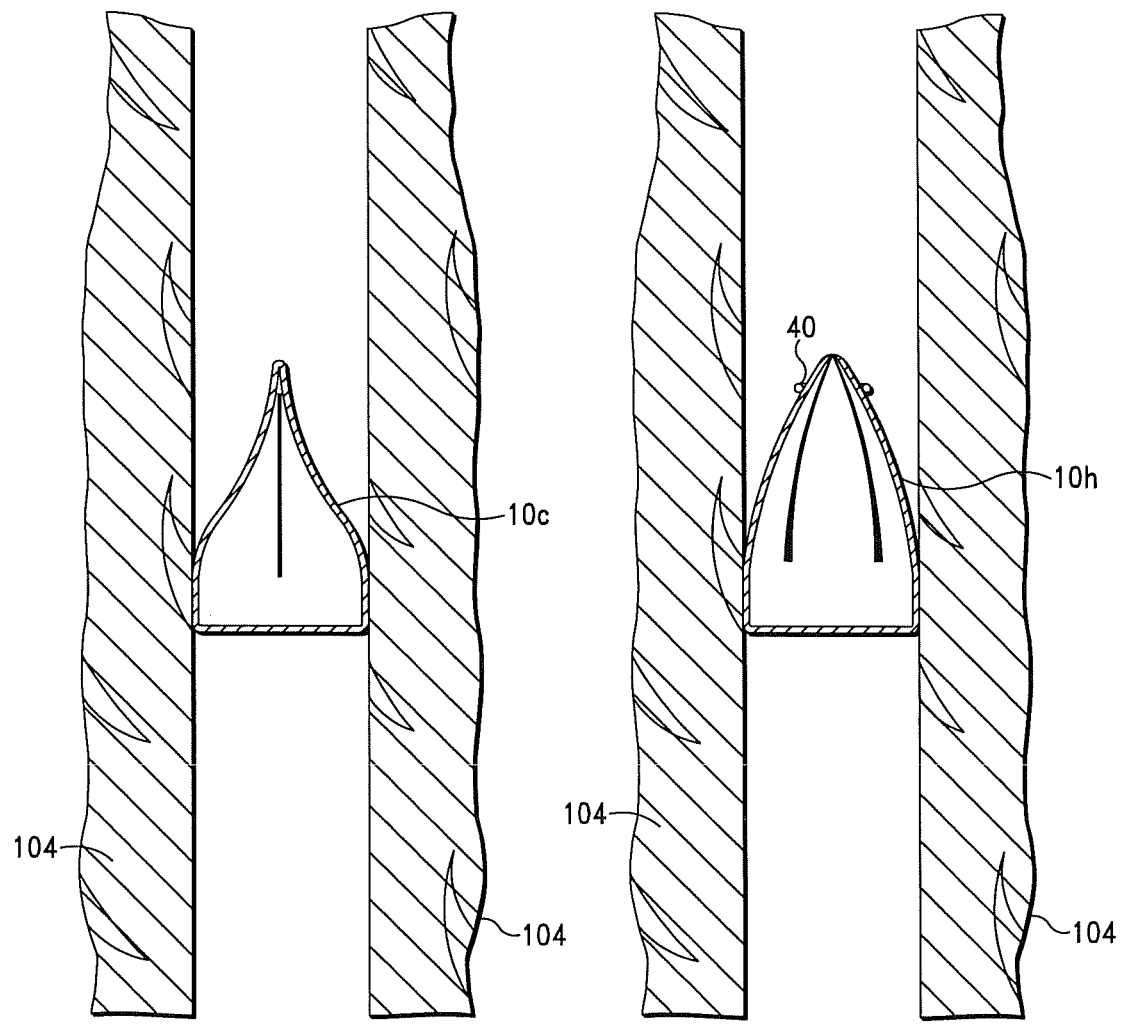
FIG. 15 is an illustration of the prosthetic "sheet structure" venous valve shown in FIG. 6A disposed in a venous vessel, in accordance with the invention.
FIG. 16 is an illustration of the prosthetic "ribbon structure" venous valve shown in FIG. 7C disposed in a venous vessel, in accordance with the invention.

As discussed in detail below, when the prosthetic venous valves of the invention are engaged in and to a venous vessel, such as illustrated in FIGS. 15 and 16, and antegrade blood flow is induced in the vessel by contraction of the skeletal muscles in the lower extremities, whereby antegrade blood exhibiting a positive antegrade fluid pressure ($B_{af}$) flows into the taper regions of the prosthetic venous valves, as discussed in detail below, the prosthetic venous valves transition from a contracted configuration to an expanded configuration, wherein the flow modulating means thereof (denoted 12a and 12b in FIGS. 5A and 5B) open and allow the antegrade blood flow to be transmitted through the valves and, thereby, into and through the vessel, and, when the skeletal muscles in the lower extremities relax, whereby the antegrade fluid pressure is reduced, the prosthetic venous valves transition from the expanded configuration to the contracted configuration, wherein the flow modulating means close and restrict retrograde blood ($B_{rf}$) from flowing into and through the valves and, hence, into and through the vessel.

Figure 5C:
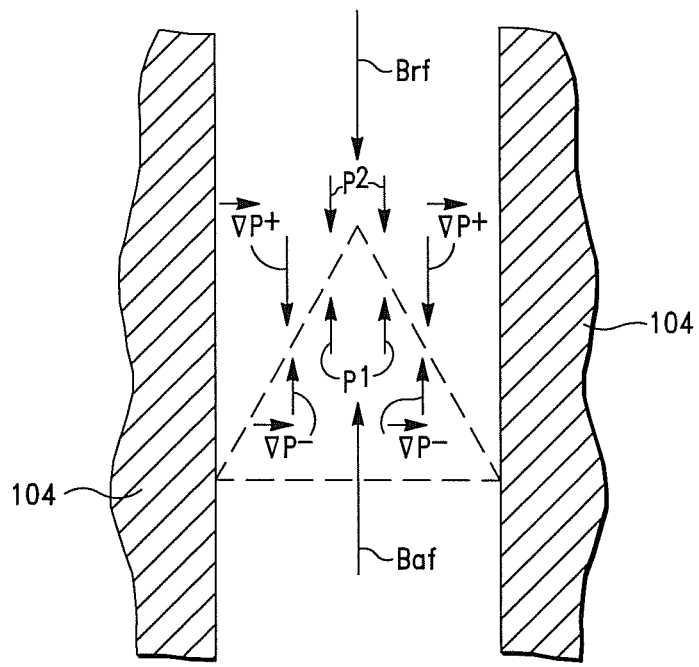
FIG. 5C is a schematic illustration of a prosthetic venous valve disposed in a venous vessel, showing the antegrade and retrograde blood flows and pressures exerted on the taper region of the valve resulting therefrom, in accordance with the invention.

Referring to FIG. 5C, according to the invention, when the prosthetic venous valves of the invention are engaged in and to a venous vessel, such as a small saphenous vein 104, and the antegrade blood exhibiting a positive antegrade fluid pressure ($B_{af}$) is directed into the taper regions of the prosthetic valves, the transition of the venous valves from the contracted configuration to the expanded configuration, and, thus opening of the flow modulating means occurs when (i) a negative hydrostatic pressure gradient (denoted "$\vec{\nabla}P^{-}$") proximate the flow modulating means is generated (and, hence, presented) and (since a hydrostatic pressure gradient is defined as a difference in pressures proximate the flow modulating means)/or (ii) a first pressure differential between the internal valvular pressure exerted proximate the interior taper region and, thereby, the flow modulating means of the prosthetic valve, (denoted "$P^{1}$") and external valvular pressure exerted proximate the exterior taper region of the prosthetic valve (denoted "$P^{2}$"), such as exerted by retrograde blood flow ($B_{rf}$), is generated.

The transition of the prosthetic venous valves of the invention from the expanded configuration to the contracted configuration, and, thus closing of the flow modulating means occurs when (i) a positive hydrostatic pressure gradient (denoted "$\vec{\nabla}P^{+}$") proximate the flow modulating means is generated (and, hence, presented), such as when a subject or patient is in an orthostatic position, and/or (ii) a second pressure differential between the internal valvular pressure ("$P^{1}$") and external valvular pressure ("$P^{2}$") is generated, the second pressure differential being lower than the first pressure differential, such as when the pressure of the antegrade blood (and, hence, flow thereof) reduces.

As also referenced above and shown in FIGS. 5A and 5B, the prosthetic venous valves of the invention comprise a conical shaped taper region. Thus, as discussed below, based on the principle of continuity, antegrade blood flowing through the conical shaped regions of the prosthetic venous valves increases in velocity as the blood flows toward the distal ends of the valves, as denoted by Arrows V at the open proximal end and V' proximate the distal ends of the valves and, hence, flow modulating means thereof.

It is well established that the velocity of the antegrade blood flow at the open proximal end of the prosthetic venous valves of the invention can be determined as follows:

$$v_1 = \frac{Q}{A_1} = \frac{Q}{\pi r_1^2} \quad \text{Eq. 1}$$

where:
- $v_1$=velocity of the antegrade blood flow at the open proximal end of the valve;
- Q=mean volumetric blood flow rate;
- $r_1$=radius of the open proximal end of the valve; and
- $A_1$=area of the open proximal end of the valve.

It is also well established that, since blood is essentially incompressible, based on the principle of continuity, the same amount of antegrade blood must flow past any point or position within the conical shaped prosthetic venous valves of the invention in any given period of time. Accordingly, the velocity of antegrade blood, i.e., the flow thereof, at any conical region position within the conical shaped prosthetic venous valves of the invention in any given period of time can thus be determined as follows:

$$v_2 = \frac{A_1}{A_2} v_1 = \frac{\pi r_1^2}{\pi r_2^2} v_1 = \frac{r_1^2}{r_2^2} v_1 \quad \text{Eq. 2}$$

where:
- $v_2$=velocity of blood proximate the distal end of the valve;
- $r_2$=radius of valve taper region proximate the distal end of the valve; and
- $A_2$=area of the distal end of the valve.

By virtue of the enhanced antegrade blood flow velocity achieved via the unique conical shape of the prosthetic venous valves of the invention, as discussed below, the prosthetic valves, when disposed in a venous vessel, will (i) provide a blood flow rate into the vessel that is at least equivalent to, and, in some instances, greater than, the blood flow into the vessel with a native venous valve, and (ii) can readily be adapted to open and direct blood into the vessel sooner than a native venous valve subjected to an equivalent antegrade blood pressure.

It is, however, well established that the velocity of antegrade blood will fluctuate based on the Newtonian classification of the blood, which, as discussed below, affects the hemodynamic conditions in the taper regions of the prosthetic venous valves of the invention, as well as inside the venous vessels to which the valves are engaged in.

As is well established, the hemodynamic conditions inside venous vessels modulate the development of at least two intraluminal stress parameters near the vessel wall; particularly, circumferential stress on the vessel wall due to pulse pressure variations inside the lumen of the vessels and wall shear stress (WSS), i.e., the stress applied by the antegrade blood against the vessel wall, due to antegrade blood flow in the lumen.

Although normal stresses due to blood pressure are transferred to all vessel wall layers, i.e., intima, media and adventitia, WSS is typically applied to the vascular endothelium, which is the inner intimal layer of the venous wall in contact with the antegrade blood flow. The normal stresses applied by blood pressure and the WSSs, regulate the vessel diameter depending on vessel wall elasticity and vascular endothelial function.

As is also well established, the determination of WSS on a surface, such as a venous vessel wall, is based on a fundamental assumption of fluid mechanics, which is that fluid particles travel parallel to the vessel wall and the velocity of the particles increases from zero to the wall at a maximum velocity value at a predetermined perpendicular distance from the wall.

Assuming that (i) the fluid traveling through a venous vessel lumen is an ideal Newtonian fluid, i.e., a fluid having a constant viscosity, (ii) the fluid flow through the vessel lumen is constant and laminar, and (iii) the vessel lumen is straight, cylindrical and inelastic, the Hagen-Poiseuille equation can be applied to determine the WSS of the vessel as follows:

$$\tau = 32 \times \left(\frac{\mu \times Q}{\pi \times d^3}\right) \quad \text{Eq. 3}$$

where:
- $\tau$=venous vessel WSS;
- $\mu$=kinetic velocity of the fluid;
- Q=mean volumetric flow rate; and
- d=diameter of the vessel.

It is, however, well established that blood flow, i.e., antegrade blood flow, through venous vessels exhibits non-Newtonian characteristics, i.e., the viscosity of the antegrade blood fluctuates based on environmental factors, such as temperature, and inherent properties of the blood, such as the concentration of red blood cells, platelets, etc.

Figure 5D:
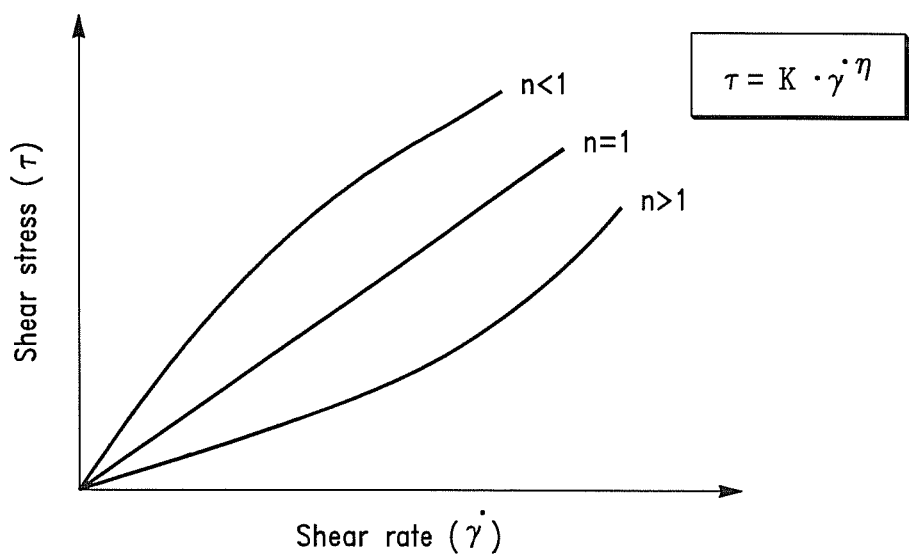
FIG. 5D is a graphical illustration of the shear stress-rate relationship for Newtonian and non-Newtonian fluids flowing into and through a venous vessel lumen.

Referring now to FIG. 5D, there is shown the shear stress-rate relationship for Newtonian fluid (denoted "n=1") and non-Newtonian fluid (denoted "n>1" and "n<1").

As illustrated in FIG. 5D, the non-Newtonian fluid characteristics of antegrade blood in a venous vessel lumen are reflected by the non-linear relationship between the vessel WSS and the shear rate ($\gamma$) of the blood—defined as the rate at which adjacent layers of fluid move with respect to each other, where shear rate is expressed as reciprocal seconds ($s^{-1}$).

Based on the fact that the antegrade blood traveling through a venous vessel lumen possesses non-Newtonian fluid characteristics, and assuming that (i) the antegrade blood flow through the vessel lumen is constant and laminar, and (ii) the vessel lumen is straight, cylindrical and inelastic, the Ostwald de Waele equation can be applied to determine the WSS ($\tau$) of the vessel as follows:

$$\tau = \kappa \times \left(\frac{32 \times Q}{\pi \times d^3}\right)^\eta \quad \text{Eq. 4}$$

where:
- $\tau$=venous vessel WSS;
- $\kappa$=antegrade blood cohesion;
- $\eta$=antegrade blood adhesion;
- Q=mean volumetric antegrade blood flow rate; and
- d=diameter of vessel.

The Ostwald de Waele equation reflects that the decrease in diameter, and, hence, cross sectional area, at the taper regions 14 of the prosthetic venous valves of the invention, e.g., valves 10a, 10b in FIGS. 5A and 5B, will amplify the WSS in the inner region thereof. For example, a 10% decrease in taper diameter is expected to increase the WSS by 33%.

According to the invention, the increase in WSS and the corresponding reduction in thrombogenicity at the valve, which is achieved by virtue of the unique conical shape of the prosthetic venous valves of the invention, is weighted against the potential increase in the pressure drop ($\Delta P$) proximate the flow modulating regions 12a, 12b (see FIGS. 5A and 5B) to overcome the resistance to flow.

Thus, in some embodiments of the invention, the length of the taper (or valve) regions of the prosthetic venous valves of the invention is optimized to achieve an optimal pressure drop ($\Delta P$) proximate the flow modulating regions and, thereby enhance blood velocity and, hence, flow.

By virtue of the enhanced blood velocity and, hence, flow achieved by virtue of the unique conical shape of the prosthetic venous valves of the invention, as indicated above, the prosthetic venous valves, when engaged to a luminal wall of a venous vessel, will provide a blood flow rate, i.e., antegrade blood flow rate, into and through the vessel lumen that is at least equivalent to, and, in some instances, greater than, the blood flow into and through the vessel lumen with a native venous valve.

The enhanced blood velocity and, hence, blood flow, i.e., antegrade blood flow, achieved by virtue of the unique conical shape of the prosthetic venous valves of the invention also advantageously results in reduced venous vessel WSS, when the prosthetic venous valves are engaged in and to a venous vessel and direct blood into the vessel.

In a preferred embodiment of the invention, when the prosthetic venous valves of the invention are engaged in a venous vessel; particularly, a vein, the vessel WSS is optimally in the range of 1-6 dyn/cm$^2$.

According to the invention, maintaining an optimal vessel WSS in the range of 1-6 dyn/cm$^2$ prevents seminal adverse pathological events that typically result from a vessel WSS outside of the noted range. As discussed below, the adverse pathological events generally relate to changes in and to the vessel morphology.

When the venous vessel WSS is >6 dyn/cm$^2$, the venous vessel wall thickness can, and often will, increase, which can, and often will, impair the ability of the smooth muscle cells in the tunica media to both contract and dilate veins to accommodate immediate changes in blood volume. A venous vessel WSS>6 dyn/cm$^2$ can also induce long-term dilation of the vessel.

A venous vessel WSS that is >6 dyn/cm$^2$ can also activate the pro-inflammatory profile of venous endothelial cells (VECs) that comprise the vascular endothelium. When the pro-inflammatory profile of VECs is activated, the VECs trigger a pro-inflammatory cascade characterized by the increased expression of pro-inflammatory cytokines, such as monocyte chemoattractant protein 1 (MCP-1), and the subsequent inducement of an adverse immune response. The noted inflammatory immune response often results in intimal hyperplasia, i.e., thickening of the intimal layer of the vessel wall.

When the venous vessel WSS is <1 dyn/cm$^2$, the vessel can, and often will contract, which can, and often will, impede blood flow therethrough. A venous vessel WSS is <1 dyn/cm$^2$ can also induce intimal hyperplasia.

Referring back to FIGS. 5A and 5B, in a preferred embodiment of the invention, the taper regions 14 of the prosthetic venous valves of the invention have a length that is at least greater than the diameter of the venous vessel (i.e., vein or other vessel/luminal organ) to prevent inversion and rotation of prosthetic venous valves when engaged therein.

In some embodiments, the length of the taper regions 14 of the prosthetic venous valves is at least three times the diameter of the venous vessel.

According to the invention, the open proximal ends of the prosthetic venous valves (denoted "11") in FIGS. 5A and 5B, preferably have a diameter in the range of approximately 5 mm to 20 mm, to accommodate virtually all cardiovascular vessels of the venous system in the lower extremities.

In a preferred embodiment, the prosthetic venous valves of the invention comprise a proximal end diameter and length ratio in the range of 5:1 to 2:1.

As discussed in detail below, in addition to the seminal advantages discussed above, the prosthetic venous valves of the invention provide numerous advantages compared to prior art prosthetic venous valves. Among the advantages are the following:

The provision of prosthetic venous valves that comprise an optimal sheet structure, including (i) increased flow modulation means (i.e., leaflet) coaptation surface area compared to conventional prosthetic valve structures, which minimizes blood flow turbulence within the valve body, and (ii) an increased flow modulation means coaptation length compared to conventional prosthetic valve structures, which, when engaged to a luminal wall of a venous vessel, decreases the likelihood of retrograde blood flow into and through the valves, and, hence, into and through venous vessels.

The provision of prosthetic venous valves that comprise a plurality of "independent" flow modulation means, whereby, if one flow modulation means is defective or fails, valve function is minimally disrupted, if at all.

The provision of prosthetic venous valves that enhance the velocity of antegrade blood flow into and through the valves and, hence, into and through venous vessels when engaged thereto.

The provision of prosthetic venous valves that can be disposed over native venous valves without resection of the native leaflets or fixing the leaflets in an open configuration.

The provision of prosthetic venous valves with minimal in vivo calcification and cytotoxicity.

The provision of prosthetic venous valves that are adapted to deliver biologically active agents, such as growth factors, and pharmacological agents, such as anti-inflammatories, to cardiovascular vessels and associated tissue, when disposed proximate thereto.

The provision of methods for replacing diseased or defective native venous valves with improved prosthetic venous valves.

As indicated above, a significant advantage of the prosthetic venous valves of the invention is that, by virtue of the increased coaptation length, when the prosthetic valves are operatively engaged to a venous vessel, the prosthetic valves (i.e., flow modulating means thereof) close more securely, which reduces the likelihood of retrograde blood flow through the valve and, hence, vessel.

As discussed in detail below, according to the invention, the prosthetic venous valves of the invention can be further adapted to close sooner than a native venous valve subjected to an equivalent antegrade blood flow pressure, which further reduces the likelihood of retrograde blood flow through the venous valve and, hence, vessel.

As is well established, peripheral venous blood pressure at the feet for a healthy adult male standing in a supine position is typically in the range of approximately 90 mm Hg to 110 mm Hg. During movement, such as walking, and, hence, muscle contraction, the pressure of antegrade blood (in the resulting antegrade blood flow) for a healthy adult male is typically in the range of 5 mm Hg to 10 mm Hg.

Thus, in a preferred embodiment of the invention, the prosthetic venous valves of the invention are configured and adapted to transition from a closed fluid flow configuration to an open fluid flow configuration when subjected to an antegrade blood flow with the antegrade blood exhibiting a pressure >3 mm Hg, whereby a pressure differential between the internal valvular pressure and external valvular pressure >1 mm Hg is generated or a negative hydrostatic pressure gradient (denoted "$\vec{\nabla}P^-$") proximate the flow modulating means is generated (or presented).

By virtue of the unique conical shaped sheet structure, the prosthetic venous valves of the invention can further be adapted to transition from the closed fluid flow configuration to the open fluid flow configuration sooner and, thereby, allow transmission of antegrade blood flow into and through an associated venous vessel sooner than a native venous valve.

In a preferred embodiment, the prosthetic venous valves are configured and adapted to transition from the closed fluid flow configuration to a fully opened fluid flow configuration when subjected to an antegrade blood flow with the antegrade blood exhibiting a pressure ≥5 mm Hg.

In a preferred embodiment of the invention, the prosthetic venous valves of the invention are further configured and adapted to transition from the open fluid flow configuration to the closed fluid flow configuration when the pressure differential between internal valvular pressure and external valvular pressure is <3 mm Hg or a positive hydrostatic pressure gradient (denoted "$\vec{\nabla}P^+$") proximate the flow modulating means is generated (or presented).

As indicated above, the prosthetic venous valves of the invention can comprise and, hence, be formed with various biocompatible materials and compositions. In a preferred embodiment, the biomaterials and compositions are employed to form sheet structures, which are then used to form the prosthetic venous valves of the invention.

In some embodiments of the invention, the prosthetic venous valves of the invention are formed from and, hence, comprise an ECM composition comprising acellular ECM from a mammalian tissue source, such as the prosthetic tissue valves disclosed in Applicant's U.S. Pat. Nos. 10,052,409, 10,188,509, 10,188,510 and 10,188,513, and Co-pending U.S. application Ser. Nos. 16/129,968, 16/440,504 and 16/553,499, which are incorporated by reference herein in their entirety.

In some embodiments of the invention, the prosthetic venous valves of the invention are formed from and, hence, comprise a polymeric composition comprising at least one polymer; preferably, a biocompatible polymer.

According to the invention, suitable biocompatible polymers include, without limitation, polyurethane urea, including porous polyurethane urea (Artelon®), polypropylene, poly(ε-caprolactone) (PCL), poly(glycerol sebacate) (PGS), polytetrafluoroethylene (PTFE), poly(styrene-block-isobutylene-block-Styrene) (SIBS), polyglycolide (PGA), polylactide (PLA), polydioxanone (a polyether-ester), polylactide-co-glycolide, polyamide esters, polyalkalene esters, polyvinyl esters, polyvinyl alcohol, polyanhydrides, polyurethanes, polydimethylsiloxanes, poly(ethylene glycol), polytetrafluoroethylene (Teflon™), and polyethylene terephthalate (Dacron™).

In some embodiments of the invention, the biocompatible polymer comprises a natural polymer.

According to the invention, suitable natural polymers include, without limitation, polysaccharides (e.g., starch and cellulose), proteins (e.g., gelatin, casein, silk, wool, etc.), and polyesters (e.g., polyhydroxyalkanoates).

In some embodiments of the invention, the polymeric composition (and, hence, prosthetic venous valves formed therefrom) further comprises at least one additional biologically active agent or composition, i.e., an agent that induces or modulates a physiological or biological process, or cellular activity, e.g., induces proliferation, and/or growth and/or regeneration of tissue.

According to the invention, suitable biologically active agents include any of the aforementioned biologically active agents, including, without limitation, the aforementioned growth factors, cells and proteins.

Thus, in some embodiments of the invention, the biologically active agent comprises a growth factor, including, without limitation, transforming growth factor beta (TGF-β), fibroblast growth factor-2 (FGF-2) (also referred to as basic fibroblast growth factor), and vascular endothelial growth factor (VEGF).

In some embodiments, the biologically active agent comprises an exosome, such as the exosomes disclosed in Applicant's priority application Ser. No. 16/129,968 and the exosomes disclosed in Applicant's U.S. Pat. No. 10,143,778 and co-pending U.S. application Ser. No. 16/990,576.

In some embodiments of the invention, the polymeric composition (and, hence, prosthetic venous valves formed therefrom) further comprises at least one pharmacological agent or composition (or drug), i.e., an agent or composition that is capable of producing a desired biological effect in vivo, e.g., stimulation or suppression of apoptosis, stimulation or suppression of an immune response, etc.

According to the invention, suitable pharmacological agents and compositions include any of the aforementioned pharmacological agents and agents set forth in Applicant's U.S. application Ser. No. 15/206,833, now U.S. Pat. No. 10,188,510.

In some embodiments of the invention, the prosthetic venous valves of the invention are formed with and, hence, comprise a collagenous tissue derived from a mammalian tissue source, i.e., a collagenous mammalian tissue.

As indicated above, the collagenous mammalian tissue can be similarly be derived from a variety of mammalian tissue sources and tissue derived therefrom, including, without limitation, the heart, small intestine, large intestine, stomach, lung, liver, kidney, pancreas, peritoneum, placenta, amniotic membrane, umbilical cord, bladder, prostate, and any fetal tissue from any mammalian organ.

In a preferred embodiment of the invention, the collagenous mammalian tissue comprises heart or cardiac tissue.

In some embodiments of the invention, the cardiac tissue comprises pericardium tissue.

In some embodiments of the invention, the mammalian tissue source comprises a bovine tissue source, e.g., bovine pericardium tissue.

In some embodiments of the invention, the mammalian tissue source comprises a porcine tissue source, e.g., porcine pericardium tissue.

In some embodiments, the mammalian tissue source comprises an adolescent mammalian tissue source, i.e., tissue derived from a mammal less than 3 years of age.

In some embodiments of the invention, the collagenous mammalian tissue is derived from a mammalian tissue source that is devoid of xenogeneic antigens.

In some embodiments, the collagenous mammalian tissue thus comprises collagenous mammalian tissue that is devoid of one of the following xenogeneic antigens: galactose-alpha-1,3-galactose (also referred to as α-gal), beta-1,4 N-acetylgalactosaminyltransferase 2, membrane cofactor protein, hepatic lectin H1, cytidine monophospho-N-acetylneuraminic acid hydroxylase, swine leukocyte antigen class I and porcine endogenous retrovirus polymerase (referred to hereinafter as "immune privileged collagenous mammalian tissue").

In some embodiments, the immune privileged collagenous mammalian tissue is derived from a genetically modified organism, such as, by way of example, a genetically modified pig and/or bovine.

In some embodiments, the immune privileged collagenous mammalian tissue is thus derived from a genetically modified pig.

In some embodiments, the genetically modified pig comprises a pig originating from at least one porcine germline cell, e.g., embryo, that has been genetically altered or reconstructed to knockout or delete at least one porcine gene that encodes for a xenogeneic antigen product.

According to the invention, the genetic alteration or reconstruction of a germline cell; more specifically, a porcine embryo can be done according to any conventional gene editing method, such as conventional gene editing methods that employ clustered regularly interspaced short palindromic repeats (CRISPR)-Cas9, Transcription Activator-like Effector Nucleases (TALEN) or RNA interference.

In some embodiments, the knockout or deletion of a gene in a porcine embryo and, hence, pig developed therefrom is done according to the CRISPR-Cas9 gene editing method described in Niu, et al., *Inactivation of Porcine Endogenous*

*Retrovirus in Pigs Using CRISPR-Cas9*, Science, vol. 357, no. 6357, pp. 1303-1307 (2017), which is incorporated by reference herein in its entirety.

According to the invention, the noted gene editing methods can be adapted and configured to knockout or delete any genes in a porcine embryo that encode for xenogeneic antigens including, without limitation, GGTA1 (galactose-alpha-1,3-galactose), β4GalNT2 (beta-1,4 N-acetylgalactosaminyltransferase 2), CD46 (membrane cofactor protein), ASGR1 (hepatic lectin H1), CMAH (cytidine monophospho-N-acetylneuraminic acid hydroxylase), SLA class I (swine leukocyte antigen class I) and PERV pol (porcine endogenous retrovirus polymerase) gene.

In a preferred embodiment, the collagenous mammalian tissue is derived from mammalian tissue of a pig developed from an embryo that has been genetically altered by knocking out or deleting the genes GGTA1, β4GalNT2 and CMAH, which encode for the xenogeneic antigen products galactose-alpha-1,3-galactose, beta-1,4 N-acetylgalactosaminyltransferase 2 and cytidine monophospho-N-acetylneuraminic acid hydroxylase, respectively.

According to the invention, the likelihood of inducing an adverse immune response, including adverse immune responses associated with xenogeneic tissue graft rejection, in vivo with the above referenced immune privileged collagenous mammalian tissue is minimal.

In some embodiments of the invention, the collagenous mammalian tissue (and, hence, prosthetic venous valve formed therefrom) further comprises at least one additional biologically active agent or composition, i.e., an agent that induces or modulates a physiological or biological process, or cellular activity.

According to the invention, suitable biologically active agents similarly include any of the aforementioned biologically active agents, including, without limitation, the aforementioned growth factors, cells and proteins.

In some embodiments of the invention, the collagenous mammalian tissue (and, hence, prosthetic venous valve formed therefrom) further comprises at least one of the aforementioned pharmacological agents and agents set forth in Applicant's U.S. application Ser. No. 15/206,833, now U.S. Pat. No. 10,188,510.

According to the invention, the collagenous mammalian tissue can comprise any suitable thickness. In some embodiments, the collagenous mammalian tissue comprises a thickness in the range of approximately 0.1 mm to 5.0 mm.

In a preferred embodiment of the invention, the collagenous mammalian tissue comprises a thickness in the range of approximately 0.2 mm to 1.0 mm.

In a preferred embodiment, the collagenous mammalian tissue comprises crosslinked collagenous mammalian tissue.

According to the invention, the collagenous mammalian tissue can crosslinked by various conventional means.

In a preferred embodiment, the collagenous mammalian tissue is crosslinked by subjecting the mammalian tissue to a suitable crosslinking agent (i.e., incubating the mammalian tissue in a suitable crosslinking agent or solution thereof), whereby the tissue exhibits bonded or crosslinked collagen fibrils and, thereby, increased tensile strength compared to natural, unprocessed mammalian tissue.

According to the invention, the collagenous mammalian tissue can be crosslinked with any suitable crosslinking agent, including, without limitation, glutaraldehyde, genipin, 1-ethyl-3-(3-dimethylaminopropyl) carbodiimide hydrochloride (EDC), nordihydroguaiaretic acid (NDGA), tannin acid, six methylene diisocyanate and glycerin.

In one embodiment of the invention, the collagenous mammalian tissue is processed, i.e., crosslinked, with glutaraldehyde (referred to herein after as "GA processed mammalian tissue"). Although GA processed mammalian tissue will typically exhibit enhanced mechanical properties; particularly, enhanced tensile strength, conventional GA processed mammalian tissue and, hence, prostheses formed therewith, will often present calcification and cytotoxicity issues in vivo.

It has, however, been found that the calcification and cytotoxicity issues associated with GA processed mammalian tissue in vivo can be addressed, i.e., substantially reduced or eliminated, by treating GA processed mammalian tissue with one or more stabilizing solutions during the glutaraldehyde processing.

In some embodiments, after treating the mammalian tissue with a 0.5% glutaraldehyde solution, the GA processed mammalian tissue is treated with an L-glutamic acid stabilizing solution. In a preferred embodiment, the L-glutamic acid stabilizing solution comprises $2.0$-$3.0*10^{-2}$ mol/L L-glutamic acid and $4.0$-$6.0*10^{-3}$ mol/L sodium borate.

Thus, in one preferred embodiment, the collagenous mammalian tissue is processed via the following steps:
(i) incubating the collagenous mammalian tissue at 37° C. in an isotonic tris-buffer, such as a solution comprising 10-50 μg/mL of RNAse and 0.2-0.5 μg/mL DNAse with 5 mM ethylenediaminetetraacetic acid (EDTA);
(ii) rinsing the collagenous mammalian tissue with phosphate buffered saline, such as Dulbecco's Phosphate Buffered Saline (DPBS);
(iii) incubating the collagenous mammalian tissue in a 0.05-0.5% glutaraldehyde (GA) solution with 5 mM EDTA in DPBS;
(iv) rinsing the collagenous mammalian tissue again with DPBS;
(v) incubating the collagenous mammalian tissue in a L-glutamic acid stabilizing solution comprising $2.0$-$3.0*10^{-2}$ mol/L L-glutamic acid and $4.0$-$6.0*10^{-3}$ mol/L sodium borate with 5 mM EDTA in DPBS; and
(vi) rinsing the collagenous mammalian tissue a final time with DPBS.

It has additionally been found that the calcification and cytotoxicity issues associated with GA processed mammalian tissue in vivo can similarly be addressed by treating the GA processed mammalian tissue with a carboxyl activating agent, such as 1-ethyl-3-(3-dimethylaminopropyl)-carbodiimide hydrochloride (EDC), dihexylcarbodiimide (DCC) and 1-ethyl-3-(4-azonia-4,4-dimethylpentyl) carbodiimide iodide (EAC), which will cause the carboxyl (COOH) groups present on the collagen molecules to be converted to activated carboxyl moieties (e.g., o-acylisourea), and immediately after treating the GA processed mammalian tissue with a carboxyl activating agent, treating the tissue with a non-carboxyl agent, such as an amine, e.g., propyl amine, ethylene diamine, etc., which reacts with the activated carboxyl moieties (e.g., o-acylisourea) formed via the carboxyl activating agent treatment to form non-carboxyl side groups on the collagen molecules in place of the previously existing carboxyl (COOH) groups.

In a preferred embodiment of the invention, the carboxyl agent comprises 1-ethyl-3-(3-dimethylaminopropyl)-carbodiimide hydrochloride (EDC) and the non-carboxyl agent comprises propyl amine.

Thus, in another preferred embodiment, the collagenous mammalian tissue is processed via the following steps:

(i) incubating the collagenous mammalian tissue at 37° C. in an isotonic tris-buffer, such as a solution comprising 10-50 µg/mL of RNAse and 0.2-0.5 µg/mL DNAse with 5 mM EDTA;

(ii) rinsing the collagenous mammalian tissue with DPBS;

(iii) incubating the collagenous mammalian tissue in a 0.05-0.5% glutaraldehyde (GA) solution with 5 mM EDTA in DPBS;

(iv) rinsing the collagenous mammalian tissue again with DPBS;

(v) incubating the collagenous mammalian tissue in a carboxyl activating agent comprising EDC;

(vi) rinsing the collagenous mammalian tissue again with DPBS;

(vii) incubating the collagenous mammalian tissue in a non-carboxyl agent comprising propyl amine; and (viii) rinsing the collagenous mammalian tissue a final time with DPBS.

According to the invention, collagenous mammalian tissue subjected to one of the aforementioned GA processing methods of the invention, i.e., GA processed mammalian tissue, will exhibit minimal cytotoxicity and calcification in vivo.

The GA processed mammalian tissue will also exhibit the following physical characteristics:

(i) a tensile strength in the range of 9.0-12.0 MPa; and (ii) an elastic phase slope, i.e., modulus (E), in the range of approximately 0.3 MPa to 0.9 MPa, depending on the incubation time of the collagenous mammalian tissue in the GA solution.

In a preferred embodiment, the collagenous mammalian tissue is incubated in the GA solution for a period of time in the range of for 24-48 hours, wherein the GA processed mammalian tissue exhibits an elastic phase slope in the range of approximately 0.3 MPa to 0.5 MPa.

In another preferred embodiment of the invention, the mammalian tissue is processed, i.e., crosslinked, with a procyanidin solution (referred to herein after as "PA processed mammalian tissue").

It has been found that procyanidin not only has the ability to stabilize extracellular matrix-derived scaffolds that primarily rely on hydrogen bonding, but also adds antioxidant and pharmacological activity to such scaffolds due to its ability to absorb free radicals.

Thus, in another preferred embodiment, the collagenous mammalian tissue is processed via the following steps:

(i) incubating the collagenous mammalian tissue at 37° C. in an isotonic tris-buffer, such as a solution comprising 10-50 µg/mL of RNAse and 0.2-0.5 µg/mL DNAse with 5 mM EDTA;

(ii) rinsing the collagenous mammalian tissue with DPBS;

(iii) incubating the collagenous mammalian tissue in a 0.1-0.5 wt % procyanidin solution with 5 mM EDTA in DPBS for a period of time in the range of 1-48 hrs; and (iv) rinsing the collagenous mammalian tissue a final time with DPBS.

In a preferred embodiment of the invention, the PA processed mammalian tissue will similarly exhibit minimal cytotoxicity and calcification in vivo. The PA processed mammalian tissue will also exhibit a tensile strength of approximately 19.0 MPa to 22.0 MPa, which is approximately 70% greater than natural, untreated mammalian tissue, and an elastic phase slope comparable to the GA processed mammalian tissue of the invention.

According to the invention, the collagenous mammalian tissue can also be sterilized according to any conventional method, such as the methods disclosed in Applicant's U.S. application Ser. No. 13/480,205, and U.S. Pat. Nos. 8,845,719, 9,226,821 and 8,877,224, which are incorporated by reference herein in their entirety.

In some embodiments of the invention, the collagenous mammalian tissue is processed or sterilized (post-GA or PA processing, or solely) via Applicant's proprietary Novasterilis™ process disclosed in U.S. Pat. Nos. 7,108,832, 8,034,288 and 8,974,730, which are incorporated by reference herein.

In some embodiments of the invention, the aforementioned supplemental biologically active agents and pharmacological agents are introduced into the collagenous mammalian tissue via Applicant's proprietary Novasterilis™ process.

Thus, as indicated above, in some embodiments of the invention, the collagenous mammalian tissue comprises at least one of the aforementioned biologically active agents and/or pharmacological agents and compositions formed therefrom.

In some embodiments of the invention, it is thus contemplated that, following placement of a prosthetic venous valve of the invention in a cardiovascular structure, such as a venous vessel, and, hence, cardiovascular tissue associated therewith, the prosthetic venous valve will induce "modulated healing" of the cardiovascular structure(s) and cardiovascular tissue associated therewith.

The term "modulated healing", as used herein, and variants of this language generally refer to the modulation (e.g., alteration, delay, retardation, reduction, etc.) of a process involving different cascades or sequences of naturally occurring tissue repair in response to localized tissue damage or injury, substantially reducing their inflammatory effect.

Modulated healing, as used herein, includes many different biologic processes, including epithelial growth, fibrin deposition, platelet activation and attachment, inhibition, proliferation and/or differentiation, connective fibrous tissue production and function, angiogenesis, and several stages of acute and/or chronic inflammation, and their interplay with each other.

For example, in some embodiments of the invention, a prosthetic venous valve of the invention is specifically formulated (or designed) to alter, delay, retard, reduce, and/or detain one or more of the phases associated with healing of damaged tissue, including, but not limited to, the inflammatory phase (e.g., platelet or fibrin deposition), and the proliferative phase when in contact with biological tissue.

In some embodiments, "modulated healing" means and includes the ability of a prosthetic venous valve of the invention to restrict the expression of inflammatory components.

By way of example, according to the invention, when a prosthetic venous valve (and/or annular ring and/or structural ring) of the invention comprises a statin and the prosthetic venous valve is positioned proximate damaged cardiovascular tissue, e.g., attached to a cardiovascular vessel, the valve restricts expression of monocyte chemoattractant protein-1 (MCP-1) and chemokine (C—C) motif ligand 2 (CCR2).

By way of further example, according to the invention, when a prosthetic venous valve comprises an immune privileged collagenous mammalian tissue, as defined herein, and the prosthetic venous valve is positioned proximate damaged cardiovascular tissue, e.g., attached to a cardiovascular vessel, the valve will not induce an adverse immune response; particularly, an immune response associated with tissue prosthesis rejection in vivo.

In some embodiments of the invention, "modulated healing" means and includes the ability of a prosthetic venous valve of the invention to alter a substantial inflammatory phase (e.g., platelet or fibrin deposition) at the beginning of the tissue healing process. As used herein, the phrase "alter a substantial inflammatory phase" refers to the ability of a prosthetic venous valve of the invention to substantially reduce the inflammatory response at a damaged tissue site, e.g., cardiovascular vessel, when in contact with tissue at the site.

The term "modulated healing" also refers to the ability of a prosthetic venous valve of the invention to induce cell migration, and cell and host tissue proliferation when disposed proximate damaged tissue.

Figure 6A:
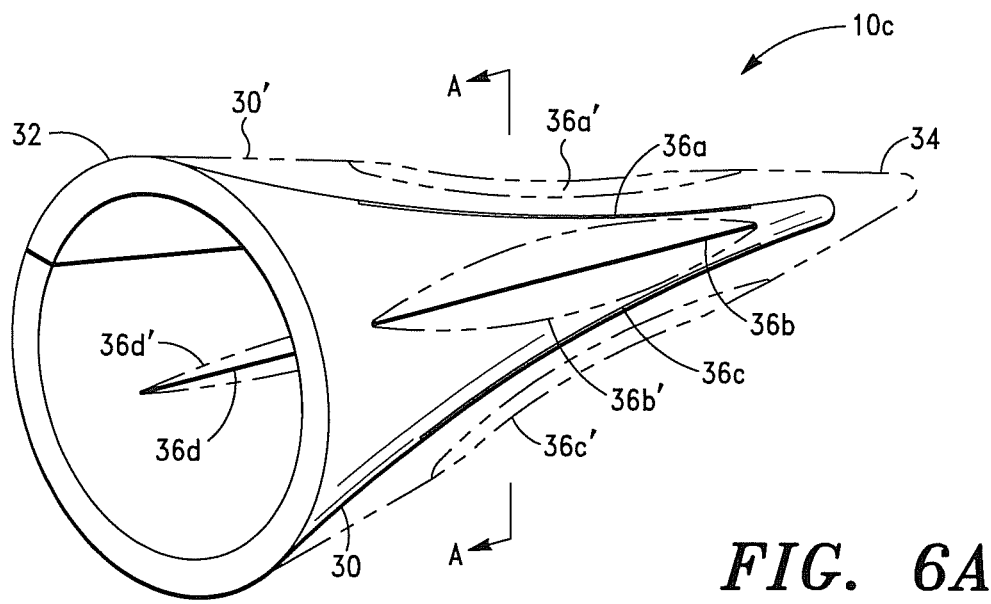
FIG. 6A is a perspective view of one embodiment of prosthetic "sheet structure" venous valve, in accordance with the invention.
Figure 6B:
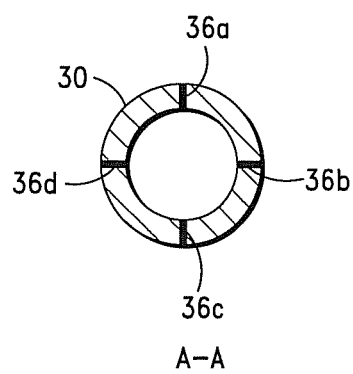
FIG. 6B is an end plane view of the prosthetic "sheet structure" venous valve shown in FIG. 6A, in accordance with the invention.

Referring now to FIGS. 6A and 6B, there is shown one embodiment of a prosthetic venous valve of the invention (denoted "10c").

As set forth in Applicant's U.S. Pat. Nos. 10,188,509 and 10,188,510, which are incorporated by reference herein, and illustrated in FIG. 6A, the prosthetic venous valve 10c comprises a continuous "sheet structure" conical shaped member 30.

As illustrated in FIG. 6A, the prosthetic venous valve 10c further comprises an open proximal end 32 and distal end 34. According to the invention, the open proximal end 32 of the valve 10c is sized and configured to engage a cardiovascular vessel.

In a preferred embodiment of the invention, the open proximal end 32 of the valve 10c (and valves 10d and 10e, discussed below) has an outer diameter in the range of approximately 5 mm to 20 mm.

According to the invention, the conical shaped member 30 and, hence, prosthetic venous valve 10c can (and valves 10d-10e) comprise any length.

In some embodiments of the invention, prosthetic venous valve 10c (and valves 10d-10e) has a length at least greater than the diameter of the venous vessel in which the valve 10c is going to be implanted in (i.e., vein or other vessel/luminal organ) to prevent inversion and rotation of valve 10c within the vessel.

In at least one embodiment, the length of prosthetic venous valve 10c is at least three times the diameter of the cardiovascular vessel.

In a preferred embodiment of the invention, the conical shaped member 30 and, hence, prosthetic venous valve 10c (and venous valves 10d-10e) has a proximal end diameter and length ratio in the range of 5:1 to 2:1.

As illustrated in FIGS. 6A and 6B, the prosthetic venous valve 10c further comprises a plurality of flow modulation means, i.e., open regions or interstices, 36a-36d that are preferably disposed linearly over a portion of the length of the member 30.

As also set forth in Applicant's U.S. Pat. Nos. 10,188,509 and 10,188,510, the length and width of the interstices 36a-36d can comprise any length or width.

In some embodiments, the interstices 36a-36d have a length that is in the range of approximately 10% to 98% of the length of the conical shaped member 30. In some embodiments, the interstices 36a-36d comprise a length that is in the range of approximately 50% to 98% of the length of the conical shaped member 30.

In a preferred embodiment, the distal ends of the interstices 36a-36d are disposed proximate the distal end 34 of the conical shaped member 30 and, hence, valve to prevent blood pooling proximate the distal end 34 of the conical shaped member 30.

According to the invention, the interstices 36a-36d can have the same length and width or different lengths and widths. In a preferred embodiment, the interstices 36a-36d have the same length and width.

As indicated above, according to the invention, the prosthetic venous valve 10c (and similar "sheet structure" venous valves of the invention, including, without limitation, "sheet structure" venous valves 10d and 10e described below) can comprise an extracellular matrix (ECM) composition and/or a polymeric composition of the invention, and a collagenous mammalian tissue derived from a mammalian tissue source.

As also indicated above, the ECM and polymeric compositions, and collagenous mammalian tissue can further comprise one of the aforementioned biologically active agents and/or pharmacological agents of the invention.

Figure 6C:
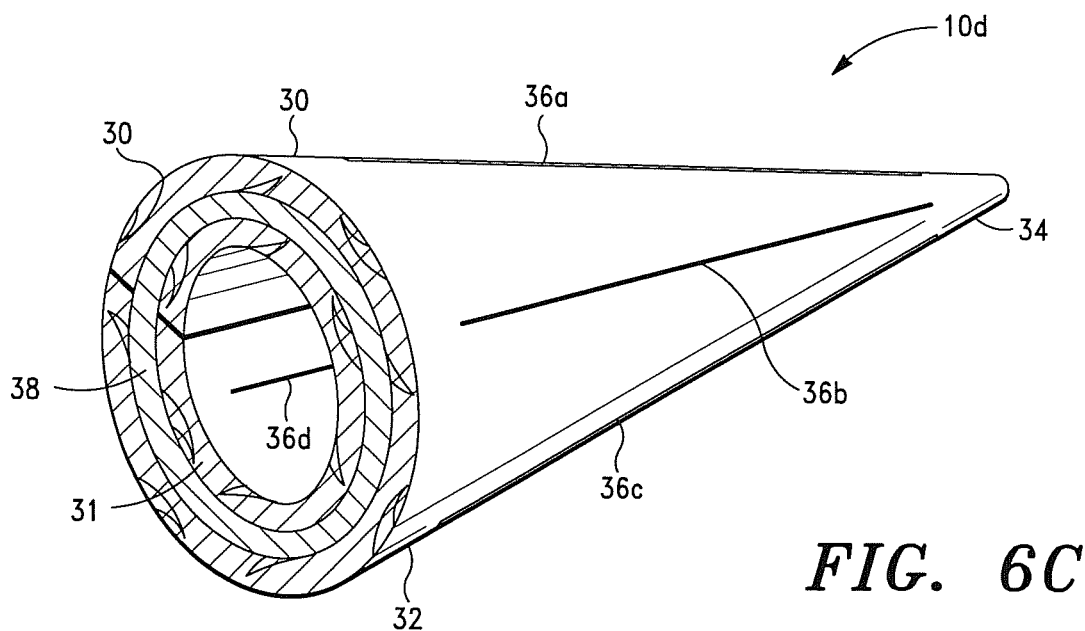
FIG. 6C is a perspective view partial sectional of another embodiment of a prosthetic "sheet structure" venous valve shown in FIG. 6A having an annular ring disposed at the open proximal end of the valve, in accordance with the invention.

Referring now to FIG. 6C, there is shown another embodiment of the prosthetic venous valve 10c that is shown in FIG. 6A. As illustrated in FIG. 6C, the prosthetic venous valve, now denoted 10d, further comprises a second (or inner) sheet member 31 and an annular ring 38.

According to the invention, the annular ring 38 is designed and configured to securely engage the prosthetic venous valve 10d to a luminal wall of a cardiovascular vessel (and, hence, cardiovascular tissue associated therewith).

As further illustrated in FIG. 6C, in a preferred embodiment, the annular ring is disposed between sheet member 30 and inner sheet member 31.

According to the invention, the outer circumference of the annular ring 38 can comprise various dimensions. In some embodiments of the invention, the ratio of the circumference of the annular ring 38 to the operative valve circumference of prosthetic venous valve 10c (and prosthetic venous valves 10d-10e) is in the range of approximately 1:1 to approximately 3:1.

Figure 6D:
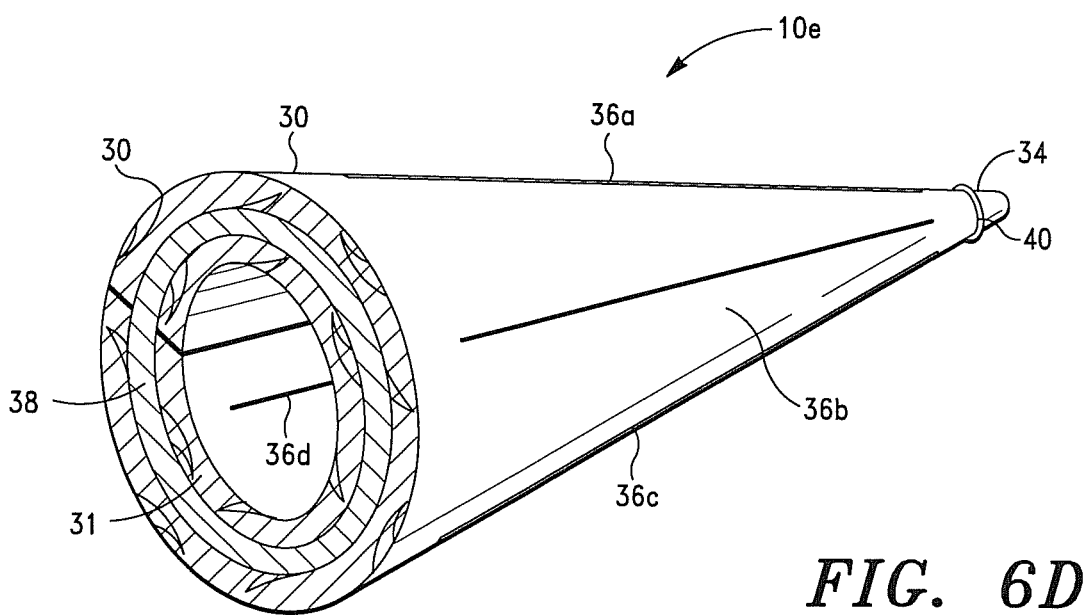
FIG. 6D is a perspective view partial sectional of yet another embodiment of a prosthetic venous valve shown in FIG. 6A having an annular ring disposed at the open proximal end of the valve and a structural ring disposed at the distal end of the valve, in accordance with the invention.

Referring now to FIG. 6D, there is shown yet another embodiment of the prosthetic venous valve 10c that is shown in FIG. 6A. As illustrated in FIG. 6D, the prosthetic venous valve, now denoted 10e, further comprises a structural ring 40 that is disposed on the distal end 34 of the valve 10e.

According to the invention, the annular ring 38 and/or structural ring 40 can comprise various biocompatible materials, such as the materials disclosed in U.S. Pat. No. 10,857,263.

In some embodiments of the invention, the annular ring 38 and/or structural ring 40 comprise a polymeric composition comprising one of the aforementioned biodegradable polymeric materials.

In some embodiments, the annular ring 38 and/or structural ring 40 comprise polyurethane urea).

In some embodiments, the annular ring 38 and/or structural ring 40 comprise poly(glycerol sebacate) (PGS).

In some embodiments, the annular ring 38 and/or structural ring 40 comprise an ECM composition comprising acellular ECM derived from one of the aforementioned mammalian tissue sources.

Figure 1B:
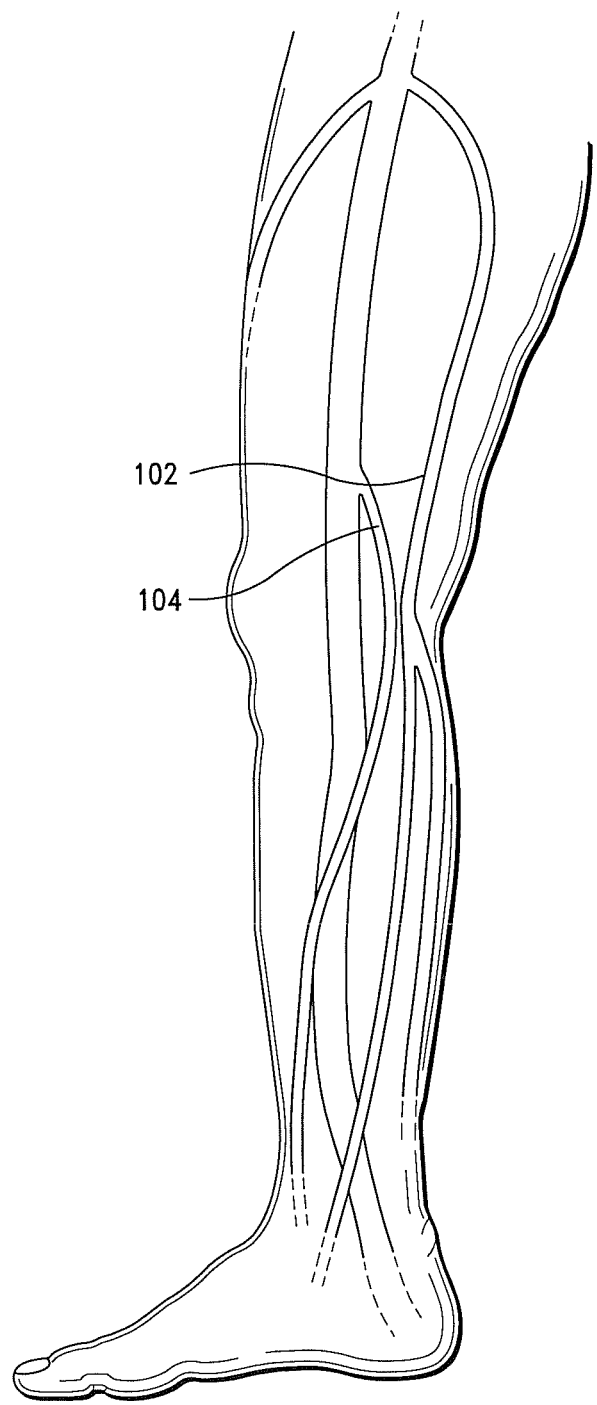
Figure 2A:
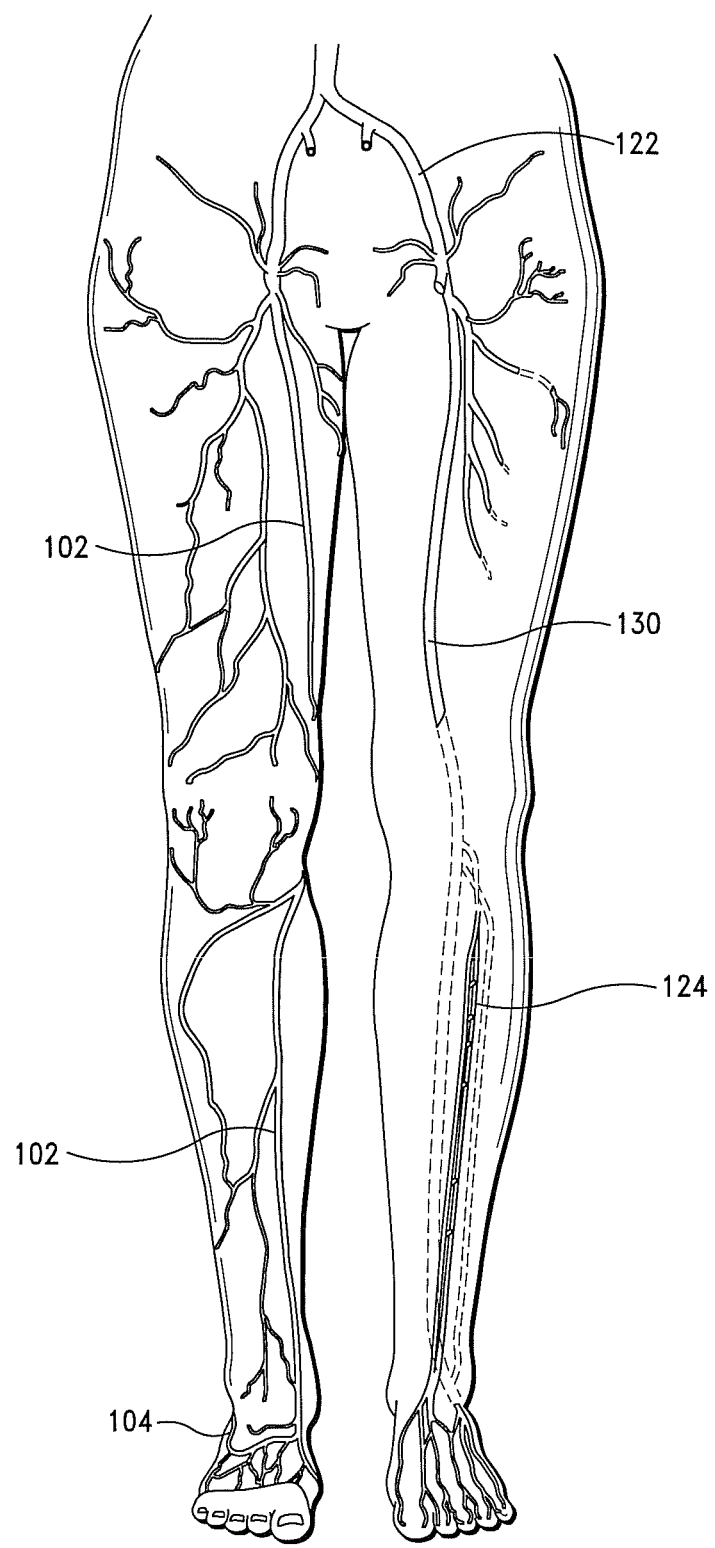
FIGS. 2A and 2B are illustrations of the deep venous system and venous vessels associated therewith.
Figure 2B:
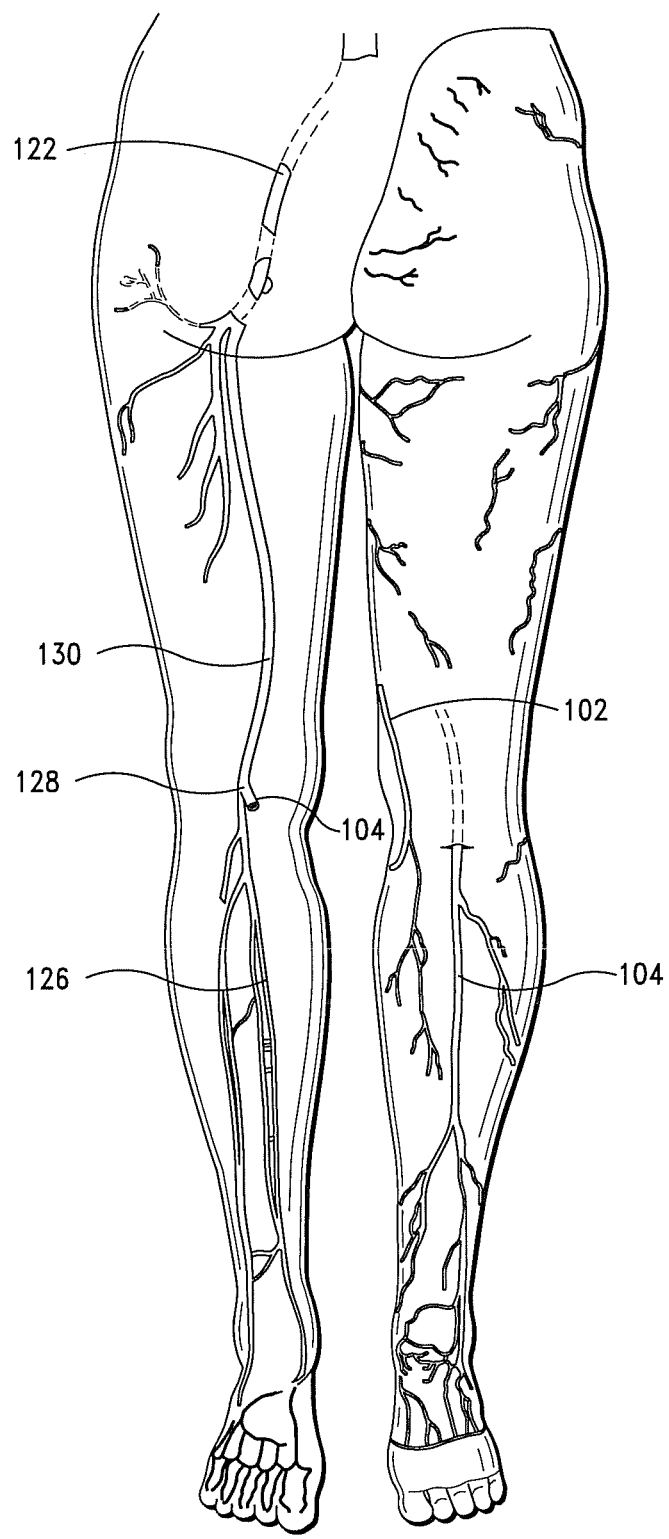

As indicated above, according to the invention, when the prosthetic "sheet structure" venous valves 10c, 10d and 10e described above are disposed in a venous vessel, such as the small saphenous vein 104 illustrated in FIGS. 1A, 1B and 15, the open proximal end 32 of the conical shaped member 30 of the "sheet structure" venous valves is engaged to a luminal wall of the venous vessel, and receives antegrade blood, i.e., blood in an antegrade blood flow, therein that exhibits a first positive fluid pressure, whereby a first positive pressure differential between first internal valvular pressure (resulting from the first positive fluid pressure) and first external valvular pressure on the sheet member 30 and, hence, "sheet structure" venous valves (or a negative hydrostatic pressure gradient) is generated, and, thereby, internal forces are exerted on the internal surface of the "sheet structure" venous valves, i.e., sheet member 30 thereof, the sheet member 30 is adapted to transition from a contracted configuration to an expanded configuration (i.e., deflect outwardly), as shown in phantom and denoted 30' in FIG. 6A, and transition from the expanded configuration to the contracted configuration during transition of the first positive pressure differential to a second pressure differential between second internal valvular pressure and second external valvular pressure, the second pressure differential being lower than the first positive pressure differential (or a positive pressure gradient is generated or presented), such as when the antegrade blood within the venous valves exhibits a second fluid pressure that is less than the first positive fluid pressure, whereby the forces exerted on the internal surface of the "sheet structure" venous valves, i.e., sheet member 30 thereof, decrease.

The interstices 36a-36d (i.e., flow modulating means) of the "sheet structure" venous valves are configured and adapted to transition from a closed (i.e., restricted) fluid flow configuration to an open (i.e., unrestricted) fluid flow configuration during the noted expansion of the conical shaped member 30' (denoted 36a', 36b', 36c' and 36d' in FIG. 6A), wherein the antegrade blood is allowed to be transmitted through the interstices 36a', 36b', 36c', 36d' and into the venous vessel, e.g., small saphenous vein 104, and transition from the open fluid flow configuration to the closed fluid flow configuration during the noted transition of the sheet member 30 from the expanded configuration to the contracted configuration, wherein retrograde blood flow through the sheet member 30 and, hence, into and through the associated venous vessel is restricted, more preferably, abated.

As indicated above, in a preferred embodiment of the invention, interstices 36a-36d are configured and adapted to transition from the closed fluid flow configuration to the open fluid flow configuration when the antegrade blood comprises a pressure ≥3 mm Hg, whereby a pressure differential between the internal valvular pressure and external valvular pressure >1 mm Hg is generated or a negative hydrostatic pressure gradient (denoted "$\vec{\nabla}P^{-}$") proximate the flow modulating means is generated (or presented).

In a preferred embodiment, the interstices 36a-36d are further configured and adapted to transition from the closed fluid flow configuration to a fully opened fluid flow configuration when subjected to an antegrade blood flow with the antegrade blood exhibiting a pressure ≥5 mm Hg.

In a preferred embodiment of the invention, the total open area of the interstices 36a', 36b', 36c', 36d' when in the fully opened fluid flow configuration is at least 2× greater than the area of (or defined by) the open proximal end 32 of sheet member 30 and, hence, valve 10c.

As also indicated above, in a preferred embodiment, the interstices 36a-36d are further configured and adapted to transition from the open fluid flow configuration to the closed fluid flow configuration and, hence, sealed configuration when the pressure differential between internal valvular pressure and external valvular pressure is <3 mm Hg or a positive hydrostatic pressure gradient (denoted "$\vec{\nabla}P^{+}$") proximate the flow modulating means is generated (or presented).

Figure 7A:
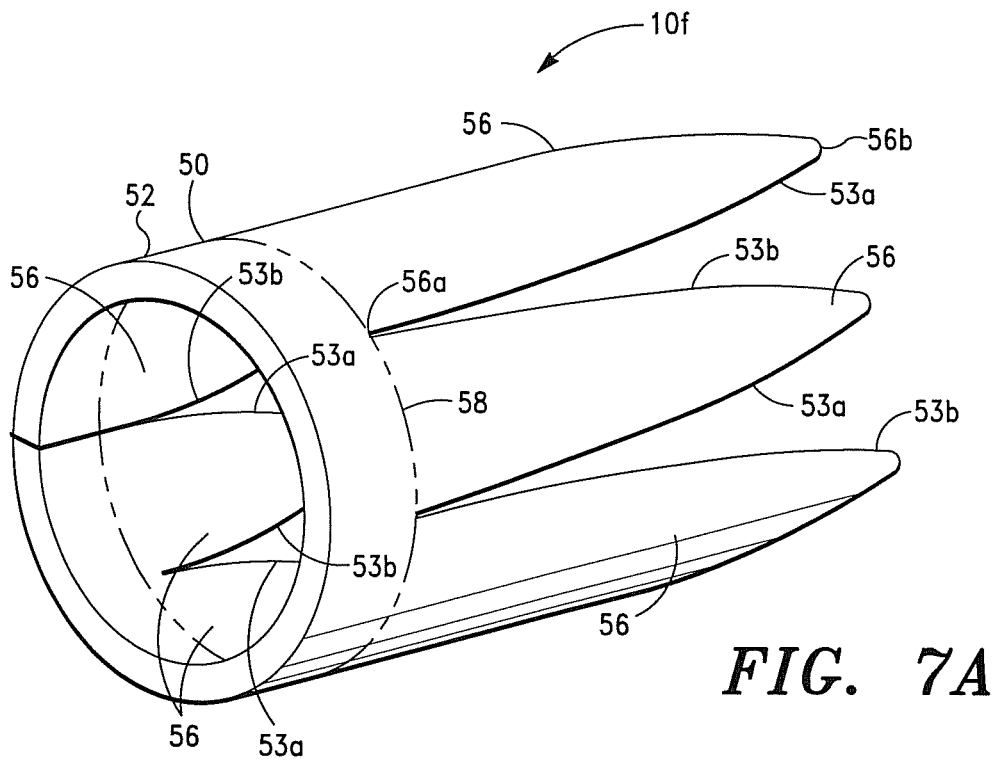
FIG. 7A is a perspective view of one embodiment of prosthetic "ribbon structure" valve, in accordance with the invention.
Figure 7B:
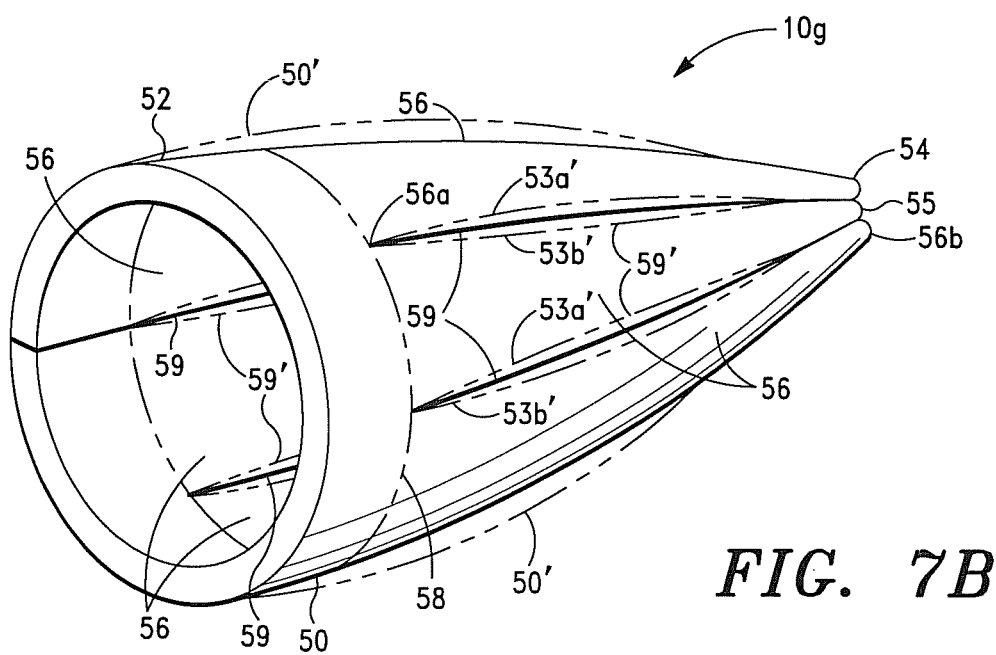
FIG. 7B is a perspective view of another embodiment of a prosthetic "ribbon structure" valve, in accordance with the invention.

Referring now to FIGS. 7A and 7B, there are shown embodiments of prosthetic "ribbon structure" valves of the invention, where FIG. 7A illustrates one embodiment of a prosthetic "ribbon structure" valve having a tubular structure, denoted 10f, and FIG. 7B illustrates one embodiment of a prosthetic "ribbon structure" valve having a conical shaped structure, denoted 10g.

As set forth in Applicant's U.S. Pat. Nos. 10,188,510 and 10,188,509, and U.S. application Ser. No. 16/129,968, which are incorporated by reference herein, prosthetic "ribbon structure" valve 10f is preferably employed to form prosthetic "ribbon structure" valve 10g.

As also set forth in Applicant's U.S. Pat. Nos. 10,188,510 and 10,188,509, and U.S. application Ser. No. 16/129,968, which are incorporated by reference herein, and illustrated in FIG. 7B, the prosthetic "ribbon structure" venous valve 10g preferably comprises a base member 50 comprising an open proximal end 52 having a circumferential ribbon connection region 58 and a distal end 54. The base member 50 further comprises a plurality of ribbon members or ribbons 56 that are connected to and extend from the ribbon connection region 58.

According to the invention, the open proximal end 52 of prosthetic "ribbon structure" venous valve 10g is similarly sized and configured to be disposed in a cardiovascular vessel, such as the small saphenous vein 104 illustrated in FIGS. 1A, 1B and 16.

According to the invention, the proximal end 52 of prosthetic "ribbon structure" venous valve 10g (and prosthetic "ribbon structure" venous valves 10h, 10j, 10k and 10m, discussed below) similarly preferably comprises an outer diameter in the range of approximately 5 mm to 20 mm.

According to the invention, prosthetic "ribbon structure" venous valve 10g (and prosthetic "ribbon structure" venous valves 10h, 10j, 10k and 10m) can also comprise any length.

In some embodiments of the invention, the prosthetic "ribbon structure" venous valve 10g (and prosthetic "ribbon structure" venous valves 10h, 10j, 10k and 10m) similarly has a taper region length at least greater than the diameter of the venous vessel in which the valve 10g is going to be implanted in (i.e., vein or other vessel/luminal organ) so to prevent inversion and rotation of prosthetic venous valve 10g within the vessel.

In at least one embodiment, the length of the taper region is at least three times the diameter of the cardiovascular vessel.

Preferably, prosthetic "ribbon structure" venous valve 10g (and prosthetic "ribbon structure" venous valves 10h, 10j, 10k and 10m) similarly has a proximal end diameter and length ratio in the range of 5:1 to 2:1.

As further illustrated in FIGS. 7A and 7B, each of the plurality of ribbons 56 preferably comprise proximal and distal ends 56a, 56b, and first and second edge regions 53a, 53b that extend from the circumferential ribbon connection region 58 to the distal ends 56b of each of the ribbons 56 and, hence, distal end 54 of the base member 50.

As illustrated in FIG. 7B, the ribbons 56 of prosthetic "ribbon structure" venous valve 10g preferably taper to a substantially coincident point 55, wherein the base member 50 has a substantially conical shape.

In a preferred embodiment, the distal ends 54 of the ribbons 56 are in a joined relationship, wherein blood flow through the joined distal ends 54 of the ribbons 56, and, hence, distal end 54 of the venous valve 10g, is restricted.

As further illustrated in FIG. 7B, the proximal ends 56a of ribbons 56 are positioned circumferentially about the circumferential ribbon connection region 58 of the base member 50, wherein the first edge regions 53a and the second edge regions 53b of the ribbons 56 are positioned adjacent each other and form a plurality of fluid flow modulating regions 59.

According to the invention, the width of the circumferential ribbon connection region 58 can be increased or extended, whereby the length of ribbons 56 and, hence, flow modulating regions 59 can be adjusted to accommodate desired blood outflow from venous valve 10g.

As indicated above, according to the invention, prosthetic "ribbon structure" venous valve 10g (and similar "ribbon structure" venous valves of the invention including, without limitation, "ribbon structure" venous valves 10h, 10j, 10k and 10m described below) can similarly comprise an extracellular matrix (ECM) composition and/or a polymeric composition of the invention, and a collagenous mammalian tissue derived from a mammalian tissue source.

As also indicated above, the ECM and polymeric compositions, and collagenous mammalian tissue can further comprise one of the aforementioned biologically active agents and/or pharmacological agents of the invention.

According to the invention, the prosthetic "ribbon structure" venous valve 10g can similarly further comprise a second (or inner) sheet member and an annular ring 38 that is designed and configured to securely engage the prosthetic valve 10g to a venous vessel (and, hence, cardiovascular tissue associated therewith), such as prosthetic "sheet structure" venous valve 10e discussed above.

Figure 7C:
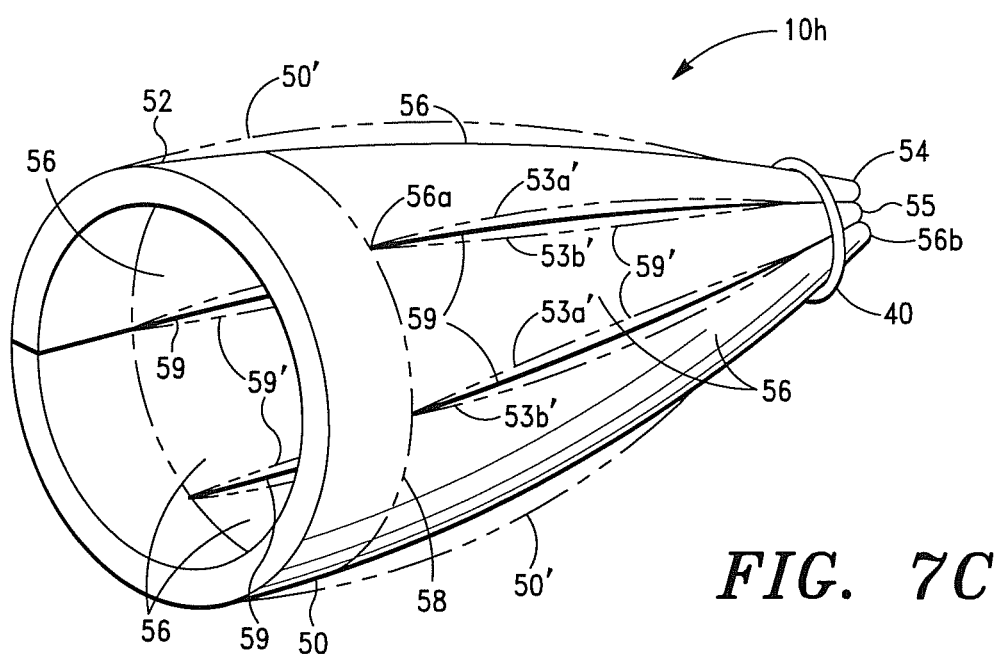
FIG. 7C is a perspective view of another embodiment the prosthetic "ribbon structure" venous valve shown in FIG. 7B having a support ring disposed at the distal end of the valve, in accordance with the invention.

Referring now to FIG. 7C, there is shown another embodiment of the prosthetic "ribbon structure" venous valve 10g that is shown in FIG. 7B. As illustrated in FIG. 7C, the prosthetic venous valve, now denoted 10h, includes a support ring 40 that is disposed on the distal end 54 of the valve 10h.

According to the invention, the structural ring 40 is preferably sized and configured to receive ribbons 56 therein in close proximity to each other, as shown in FIG. 7C.

As indicated above, the annular ring 38 and/or structural ring 40 comprise a polymeric composition comprising one of the aforementioned biodegradable polymeric materials and compositions, as well as one of the aforementioned ECM compositions.

Figure 8A:
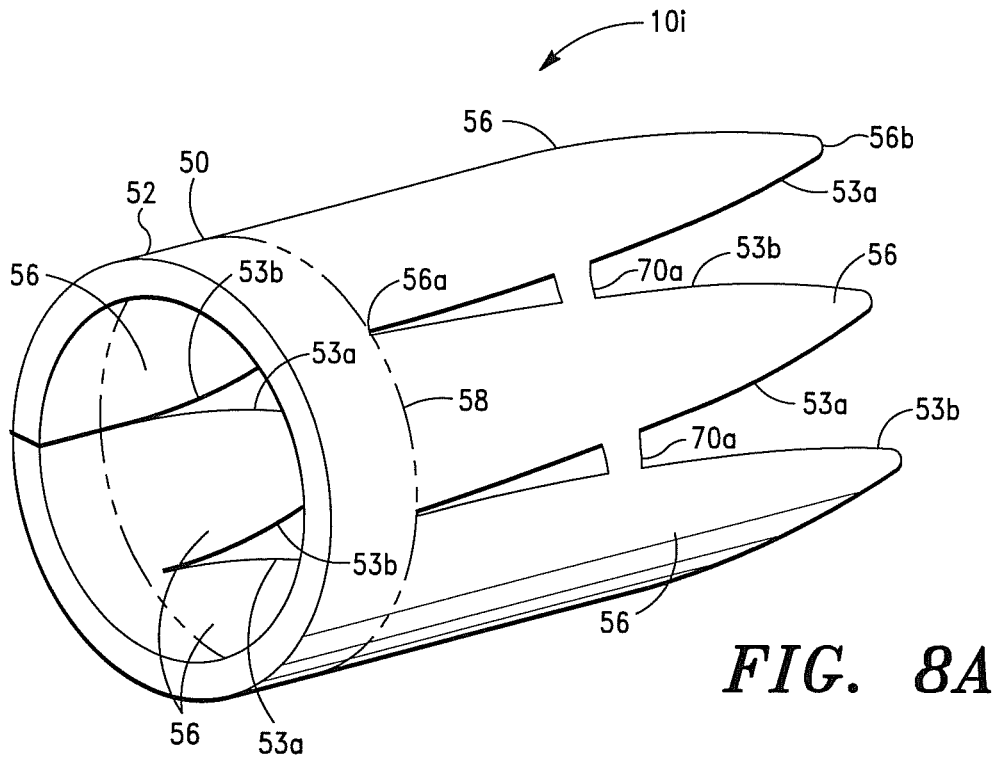
FIG. 8A is a perspective view of another embodiment of a prosthetic "ribbon structure" venous valve having an integral ribbon coupling member, in accordance with the invention.
Figure 8B:
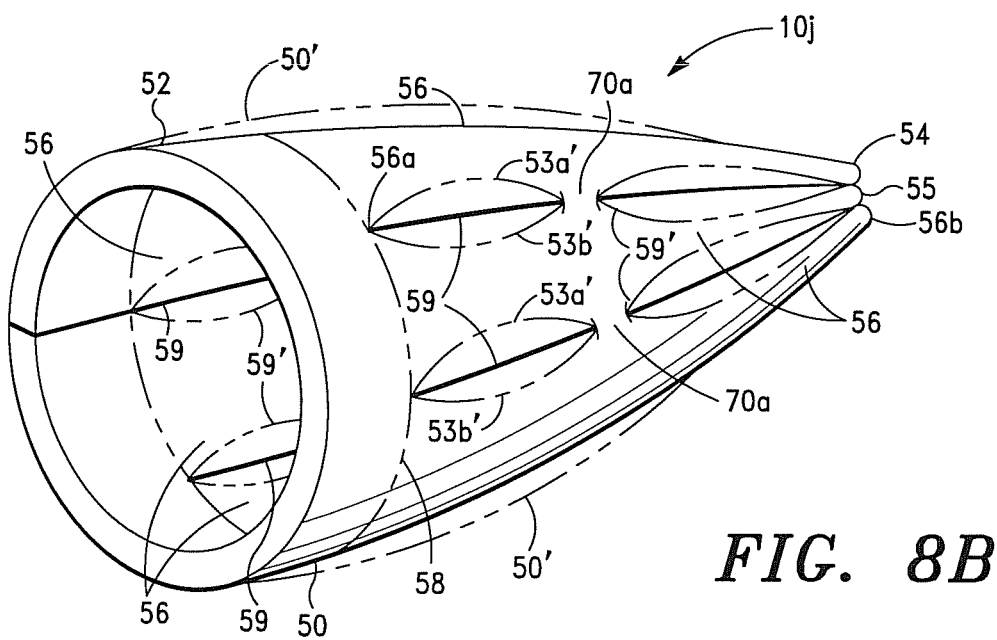
FIG. 8B is a perspective view of another embodiment of a prosthetic "ribbon structure" valve having an integral ribbon coupling member, in accordance with the invention.

Referring now to FIGS. 8A and 8B there are shown further embodiments of prosthetic "ribbon structure" valves, where FIG. 8A illustrates a prosthetic "ribbon structure" valve in a pre-operational configuration, denoted 10i, and FIG. 8B illustrates the prosthetic "ribbon structure" valve 10i in an operational configuration, denoted 10j.

As set forth in Applicant's Co-pending U.S. application Ser. No. 16/129,968, which is incorporated by reference herein, and illustrated in FIG. 8B, the prosthetic venous valve 10j also preferably comprises a base member 50 comprising an open proximal end 52 having a circumferential ribbon connection region 58, and a distal end 54. The base member 50 similarly further comprises a plurality of ribbon members or ribbons 56 that are connected to and extend from the ribbon connection region 58.

As further illustrated in FIGS. 8A and 8B, the prosthetic "ribbon structure" venous valve 10i further preferably comprises a plurality of constraining bands or coupling members 70a. According to the invention, the coupling members 70a are sized and configured to couple (or join) a ribbon 56 to adjacent ribbons, i.e., couple a first edge region 53a of a first ribbon 56 to the second edge region 53b of a second ribbon 56, at a predetermined region.

According to the invention, the coupling members 70a can be disposed at any region between the proximal and distal ends 56a, 56b of the ribbons 56.

According to the invention, the coupling members 70a can comprise separate or integral members.

As indicated above, according to the invention, the prosthetic venous valve 10i can similarly comprise an extracellular matrix (ECM) composition and/or a polymeric composition of the invention, and a collagenous mammalian tissue derived from a mammalian tissue source.

As also indicated above, the ECM and polymeric compositions, and collagenous mammalian tissue can further comprise one of the aforementioned biologically active agents and/or pharmacological agents of the invention.

Figure 8C:
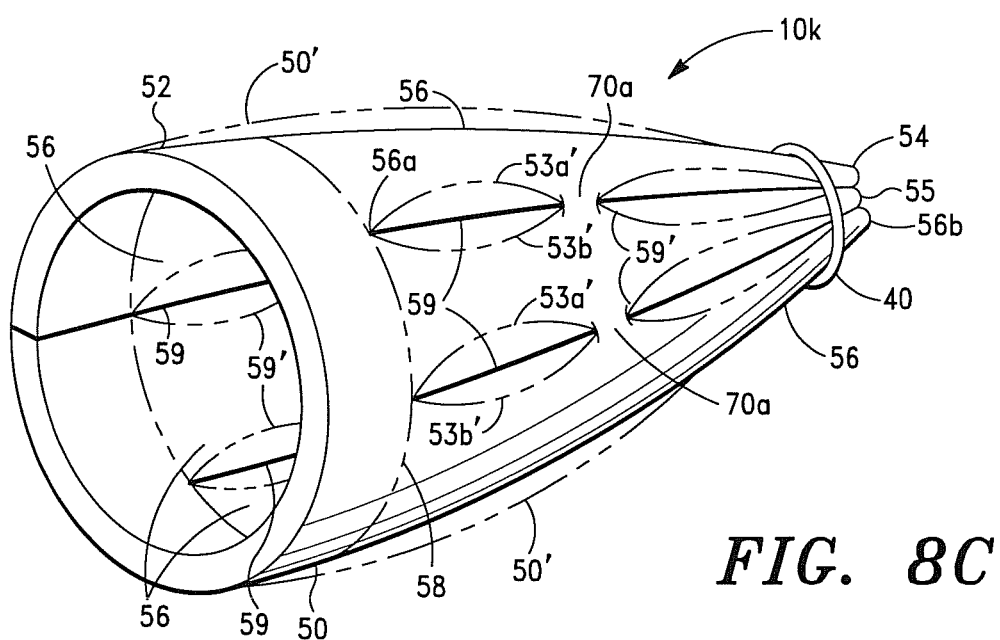
FIG. 8C is a perspective view of another embodiment the prosthetic "ribbon structure" venous valve shown in FIG. 8B having a support ring disposed at the distal end of the valve, in accordance with the invention.

Referring now to FIG. 8C, there is shown another embodiment of the prosthetic "ribbon structure" venous valve 10j that is shown in FIG. 8B. As illustrated in FIG. 8C, the prosthetic venous valve, now denoted 10k, also similarly comprises a structural ring 40, such as described above, which is disposed on the distal end 54 of the valve 10k.

As indicated above, according to the invention, when the prosthetic "ribbon structure" venous valves described above are disposed in a venous vessel, such as the small saphenous vein 104 illustrated in FIGS. 1A, 1B and 16, and the open proximal end 52 of the base member 50 of the prosthetic "ribbon structure" venous valves is engaged to a luminal wall of the vessel and receives antegrade blood, i.e., blood in an antegrade blood flow, therein that exhibits a first positive fluid pressure, whereby a first positive pressure differential between first internal valvular pressure (resulting from the first positive fluid pressure) and first external pressure (or a negative hydrostatic pressure gradient) is similarly generated and, hence, internal forces are similarly exerted on the internal surface of the "ribbon structure" venous valves, i.e., base member 50 thereof, and, hence, flow modulating regions 59, the base member 50 is similarly adapted to transition from a contracted configuration to an expanded configuration, whereby the flow modulating regions 59 (i.e., ribbons 56) deflect outwardly to an open (i.e., unrestricted) fluid flow configuration, as shown in phantom and denoted 50' in FIG. 7B, i.e., the first and second edge regions 53a, 53b separate, as shown in phantom and denoted 53a', 53b', whereby the antegrade blood is allowed to be transmitted through the flow modulating regions 59 and, hence, base member 50, and into and through the vessel.

The base member 50 is further similarly adapted to transition from the expanded configuration to the contracted configuration, whereby the ribbons 56 deflect inwardly and the flow modulating regions 59 transition from the open fluid flow configuration to a closed (i.e., restricted) fluid flow configuration during transition of the first positive pressure differential to a second pressure differential between second internal valvular pressure and second external pressure, the second pressure differential being lower than the first positive pressure differential (or a positive hydrostatic pressure gradient is generated or presented), wherein retrograde blood through the flow modulating regions 59 and, hence, base member 50 (and, thereby, into and through the vessel) is restricted.

As indicated above, in a preferred embodiment of the invention, the flow modulating regions 59 (i.e., ribbons 56) are similarly configured and adapted to transition from the closed fluid flow configuration to the open fluid flow configuration when the antegrade blood comprises a pressure ≥3 mm Hg, whereby a pressure differential between the internal valvular pressure and external valvular pressure >1 mm Hg is generated or a negative hydrostatic pressure gradient (denoted "$\vec{\nabla}P^-$") proximate the flow modulating means is generated or presented.

In a preferred embodiment, the flow modulating regions 59 (i.e., ribbons 56) are further configured and adapted to transition from the closed fluid flow configuration to a fully opened fluid flow configuration when subjected to an antegrade blood flow with the antegrade blood exhibiting a pressure ≥5 mm Hg.

In a preferred embodiment, the total open area of the flow modulating regions 59' when in the fully opened flow configurations is similarly at least 2× greater than the area of (or defined by) the open proximal end 52 of the base member and, hence, venous valve 10g.

As also indicated above, in a preferred embodiment, the flow modulating regions 59 (i.e., ribbons 56) are further configured and adapted to transition from the open fluid flow configuration to the closed fluid flow configuration and, hence, sealed configuration when the pressure differential between internal valvular pressure and external valvular pressure is <3 mm Hg or a positive hydrostatic pressure gradient (denoted "$\vec{\nabla}P^+$") proximate the flow modulating means is generated or presented.

In some embodiments of the invention, the prosthetic "ribbon structure" venous valves of the invention further comprise a supplemental support structure, such as described in Applicant's U.S. application Ser. No. 15/206,871, now U.S. Pat. No. 10,188,513, which is also incorporated by reference herein.

As set forth in U.S. Pat. No. 10,188,513, in some embodiments of the invention, the support structure comprises a biocompatible multi-link stent structure.

Figure 9:
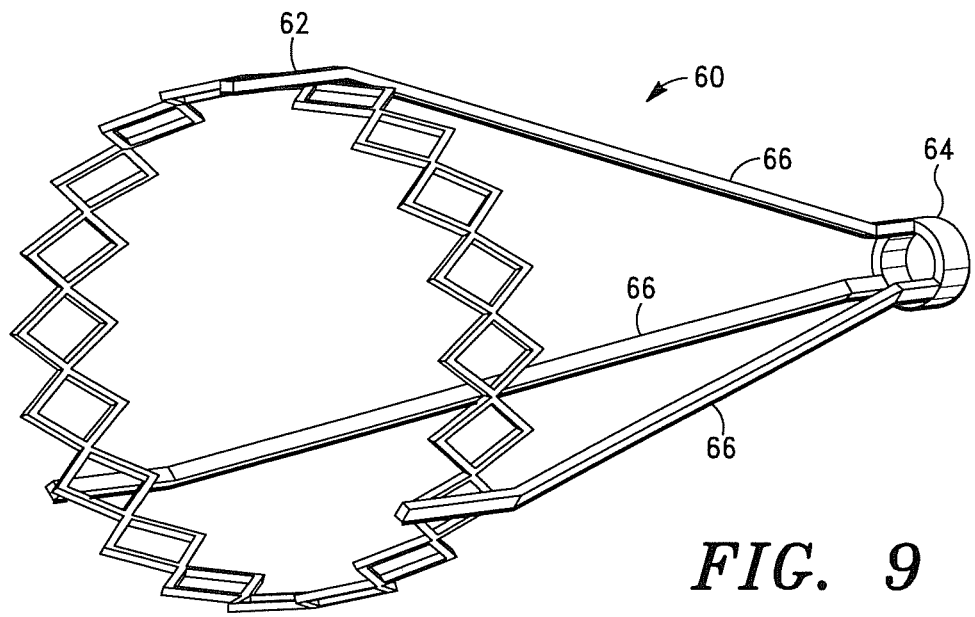
FIG. 9 is a perspective view of one embodiment of a prosthetic venous valve support structure, in accordance with the invention.

Referring now to FIG. 9, there is shown one embodiment of a prosthetic venous valve internal multi-link support structure of the invention (denoted "60").

As illustrated in FIG. 9, the multi-link support structure 60 comprises a cross-linked circumferential proximal end region 62, a cylindrical distal end region 64, and a plurality of links 66 positioned and configured to connect the cross-linked circumferential proximal end region 62 to the cylindrical distal end region 64.

According to the invention, the links 66 can comprise separate components or integral components of the support structure 60. The cylindrical distal end region 64 can also comprise a solid region, as shown in FIG. 9, or a cross-linked region similar to the cross-linked circumferential proximal end region 62.

According to the invention, the cross-linked circumferential proximal end region 62 can comprise various diameters. In some embodiments of the invention, the outer diameter of the cross-linked circumferential proximal end region 62 is in the range of approximately 5 mm to 20 mm.

In some embodiments of the invention, the ratio of the outer diameter of the cross-linked circumferential proximal end region 62 to the length of the structure 60 is similar to the ratio of the proximal end diameter and length of prosthetic "sheet structure" and "ribbon structure" venous valves, i.e., in the range of approximately 5:1 to 2:1.

In some embodiments of the invention, the ratio of the circumference of the cross-linked proximal end region 62 to the operative valve circumference (proximate the open proximal end) is similar to the ratio of the annular ring 30 to the operative valve circumference, i.e., in the range of approximately 1:1 to 3:1.

According to the invention, the multi-link support structure 60 can comprise various biocompatible materials, including, without limitation, one of the aforementioned biocompatible metals, e.g., Nitinol™, stainless steel and magnesium, and polymeric compositions.

In some embodiments of the invention, the multi-link support structure 60 comprises a polymeric composition comprising poly(urethane urea); preferably, Artelon® distributed by Artimplant AB in Goteborg, Sweden.

In some embodiments, the multi-link support structure 60 comprises a polymeric composition comprising poly(glycerol sebacate) (PGS).

Referring now to FIGS. 10 and 12-14, there are shown embodiments of prosthetic venous valves, denoted 10l and 10m, incorporating the internal multi-link support structure 60 shown in FIG. 9.

Figure 10:
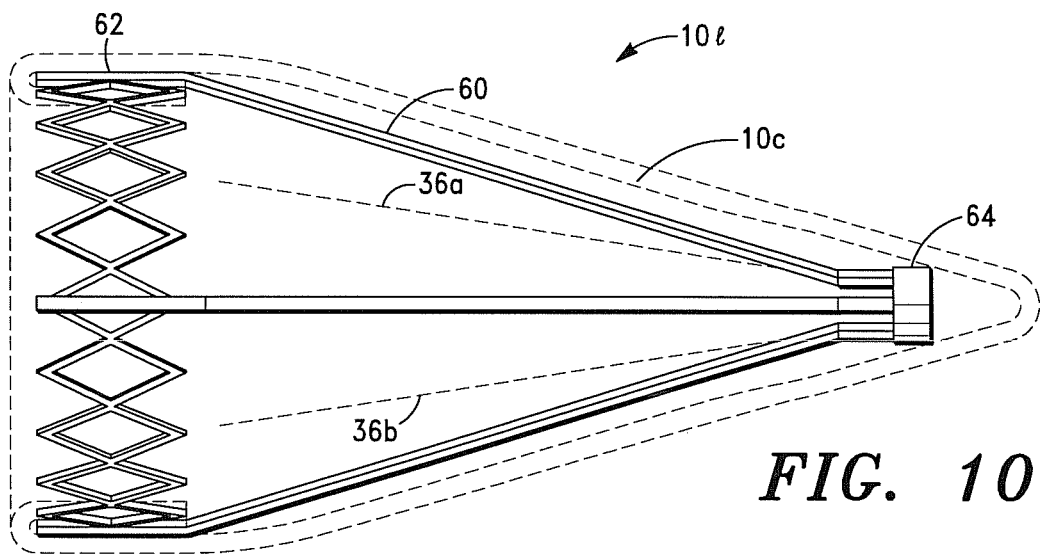
FIG. 10 is a side plan view of one embodiment of a prosthetic venous valve employing the support structure shown in FIG. 9, in accordance with the invention.
Figure 12:
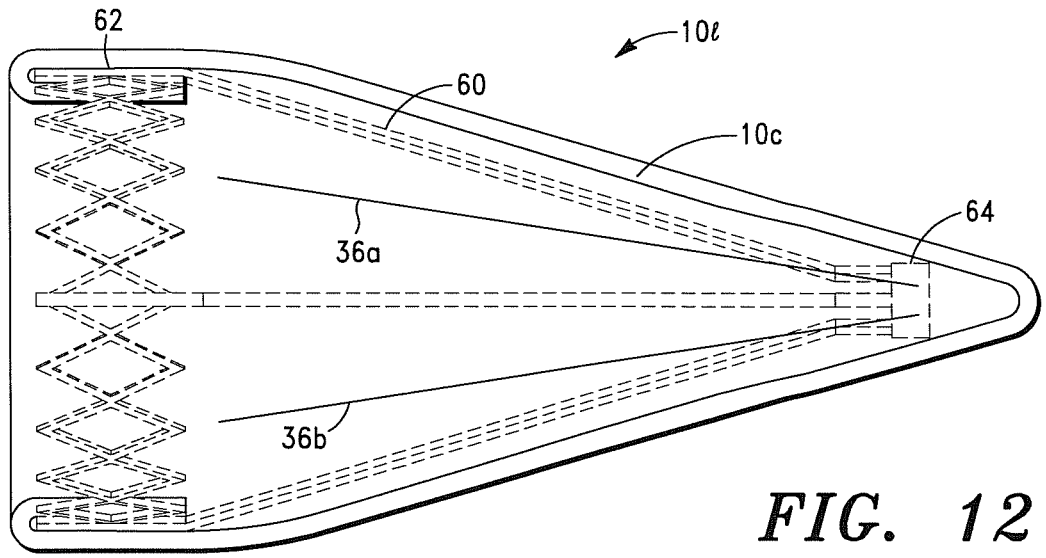
FIG. 12 is a side plan sectional view of the prosthetic venous valve shown in FIG. 10, in accordance with the invention.

As illustrated in FIGS. 10 and 12, prosthetic venous valve 10l comprises valve 10c described above (or a similar "sheet structure" valve construct, such as venous valves 10d and 10e described above) with the internal multi-link support structure 60 disposed therein.

Figure 13:
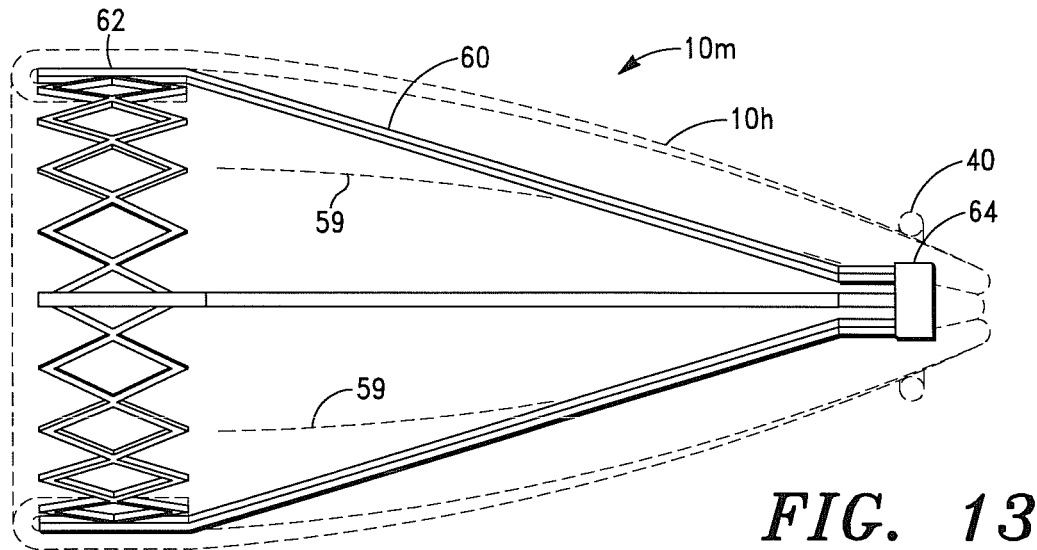
FIG. 13 is a side plan view of another embodiment of a prosthetic venous valve employing the support structure shown in FIG. 9, in accordance with the invention.
Figure 14:
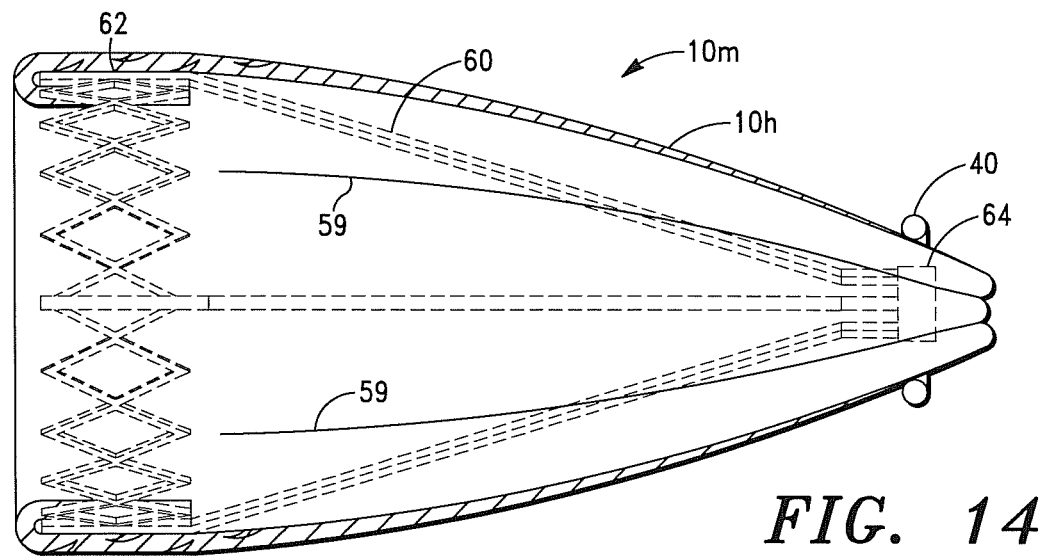

As illustrated in FIGS. 12-13, prosthetic venous valve 10m comprises valve 10h described above (or a similar "ribbon structure" valve construct, such a venous valves 10g and 10j described above) with the internal multi-link support structure 60 disposed therein.

Figure 11:
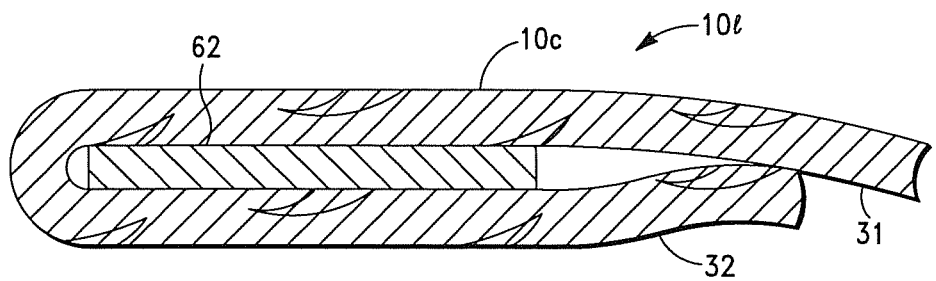
FIG. 11 is partial sectional side plan view of the prosthetic venous valve shown in FIG. 10 showing the proximal end of the valve wrapped inwardly around the proximal end of the support structure shown in FIG. 9, in accordance with the invention.

As illustrated in FIG. 11, in some embodiments of the invention, the proximal end of prosthetic "sheet structure" and "ribbon structure" venous valves 10c, 10h (i.e., open proximal valve ends 32, 52) and, hence, venous valves 10l and 10m, are secured to the cross-linked circumferential proximal end region 62 by folding the proximal ends 32, 52 of valves 10c, 10h inwardly (i.e., in the valve lumen) and securing the proximal ends 32, 52 to the inner surface 31 of the valves 10c, 10h.

In some embodiments of the invention, the open proximal ends 32, 52 of venous valves 10c, 10h and, hence, venous valves 10l and 10m, are secured to the inner surface 31 of the valves, wherein at least one valve leaflet is formed, such as disclosed in U.S. Pat. No. 10,188,513 and Applicant's U.S. application Ser. No. 15/206,902.

As indicated above, according to the invention, the "ribbon structure" venous valve 10g (and similar "ribbon structure" venous valves of the invention) can similarly comprise an extracellular matrix (ECM) composition and/or a polymeric composition of the invention, and a collagenous mammalian tissue derived from a mammalian tissue source.

In some embodiments of the invention, the prosthetic venous valves of the invention preferably comprise cross-linked collagenous mammalian tissue, more preferably, crosslinked pericardium tissue that is processed via one of the aforementioned GA processing methods of the invention, wherein the GA processed crosslinked pericardium tissue exhibits a tensile strength in the range of in the range of 9.0 MPa to 12.0 MPa and an elastic phase slope, i.e., modulus (E), in the range of approximately 0.3 MPa to 0.5 MPa.

Referring now to FIGS. 15 and 16, there are shown prosthetic "sheet structure" venous valve 10c and prosthetic "ribbon structure" venous valve 10h, respectively, engaged to a luminal wall of a venous vessel of a subject, in this instance the small saphenous vein 104.

According to the invention, the open proximal end of the prosthetic "sheet structure" and "ribbon structure" venous valves of the invention can be secured to a cardiovascular vessel by any conventional method and means, e.g., suturing.

In a preferred embodiment of the invention, the prosthetic venous valves of the invention are implanted in a cardiovascular vessel percutaneously.

According to the invention, the prosthetic venous valves of the invention can be disposed over native venous valves without resection of the native leaflets or fixing the leaflets in an open configuration.

In at least one embodiment, a prosthetic venous valve of the invention is initially placed on a valve insertion device, such as the device illustrated in U.S. application Ser. No. 12/487,501 (which is incorporated by reference herein in its entirety), in a first, or collapsed, configuration.

A guidewire, having an optional compliant end, is then inserted into the target venous vessel of a patient, such the small saphenous vein 104 shown in FIGS. 15 and 16. The insertion device with the prosthetic venous valve connected thereto is then advanced over the guidewire to a desired location within the vessel.

The distal end of the insertion device is then expanded, e.g., balloon of the insertion device is expanded, whereby the prosthetic venous valve is expanded and the open proximal end of the valve is placed in intimate contact with the walls of the venous vessel.

In accordance with one embodiment of the invention there is thus provided a prosthetic venous valve for modulating blood flow through a cardiovascular vessel, the prosthetic venous valve comprising:

a base valve member comprising an internal region, an open proximal valve member end and a distal valve member end, the open proximal valve member end being configured and adapted to engage the cardiovascular vessel, receive an antegrade blood flow therein and direct the antegrade blood flow into the internal region of the base valve member, the open proximal valve member end defining an open valve inlet end comprising a first open area, the base valve member further comprising a plurality of elongated ribbon members that extend from the open proximal valve member end of the base valve member to the distal valve member end of the base valve member, each of the plurality of elongated ribbon members comprising first and second edge regions and proximal and distal ends, the plurality of elongated ribbon members being positioned circumferentially about the base valve member, wherein the first edge regions of the plurality of elongated ribbon members are positioned proximate the second edge regions of the plurality of elongated ribbon members and form a plurality of contiguous ribbon edge regions, the plurality of contiguous ribbon edge regions forming a plurality of flow modulating regions, the distal ends of the plurality of ribbon members being positioned proximate each other in a constrained relationship, wherein the base valve member comprises a conical shaped region and the fluid flow through the constrained distal ends of the plurality of elongated ribbon members is restricted, the plurality of elongated ribbon members being configured and adapted to deflect outwardly, whereby each of the plurality of flow modulating regions transition from a restricted (or closed) fluid flow configuration to an open fluid flow configuration and allows first antegrade blood of the antegrade blood flow to be transmitted through and out of the base valve member and, thereby, into and through the cardiovascular vessel when the base valve member is engaged to the cardiovascular vessel, the open proximal valve member end of the base valve member directs the antegrade blood flow into the internal region of the base valve member and the first antegrade blood of the antegrade blood flow comprises a first positive fluid pressure ≥3 mm Hg, whereby a first positive pressure differential between first internal valvular pressure (resulting from the first positive fluid pressure) and first external valvular pressure on the base member is generated proximate the plurality of elongated ribbon members or a negative hydrostatic pressure gradient is present proximate the plurality of elongated ribbon members, the plurality of elongated ribbon members being further configured and adapted to deflect inwardly, whereby each of the flow modulating regions transitions from the open fluid flow configuration to the restricted fluid flow configuration and restricts retrograde blood flow through the base valve member and, thereby, into and through the cardiovascular vessel when the first positive pressure differential transitions to a second pressure differential between second internal valvular pressure and second external valvular pressure on the base member, the second pressure differential being lower than the first positive pressure differential, or a positive hydrostatic pressure is present proximate the plurality of elongated ribbon members.

In another embodiment of the invention there is provided a prosthetic venous valve for modulating blood flow through a cardiovascular vessel, the prosthetic venous valve comprising:

a base valve member comprising a taper region, an internal region, an exterior region, an open proximal valve member end and a closed distal valve member end, the open proximal valve member end being configured and adapted to engage the cardiovascular vessel, receive antegrade blood flow therein and direct the antegrade blood flow into the internal region of the base valve member, the open proximal valve member end defining an open valve inlet end comprising a first open area, the base valve member further comprising a plurality of linear interstices disposed in the taper region of the base valve member between the open proximal valve member end and the closed distal valve member end, the base valve member, when engaged to the cardiovascular vessel, being configured and adapted to expand and transition from a contracted configuration to an expanded configuration when the open proximal valve member end of the base valve member directs the antegrade blood flow into the internal region of the base valve member, and first antegrade blood of the antegrade blood flow comprises a first positive fluid pressure ≥3 mm Hg, whereby a first positive pressure differential between first internal valvular pressure (resulting from the first positive fluid pressure) and first external valvular pressure is generated proximate the taper region of the base valve member and, thereby, the plurality of linear interstices or a negative hydrostatic pressure gradient is present proximate the plurality of linear interstices, the plurality of linear interstices being configured and adapted to transition from a restricted fluid flow configuration to an unrestricted fluid flow configuration, wherein the plurality of linear interstices allows the antegrade blood flow to be transmitted through and out of the base valve member and, thereby, into and through the cardiovascular vessel, when the base valve member expands and transitions from the contracted configuration to the expanded configuration, the base valve member being further configured and adapted to transition from the expanded configuration to the contracted configuration when the first positive pressure differential transitions to a second pressure differential between second internal valvular pressure and second external valvular pressure, the second pressure differential being lower than the first positive pressure differential, or a positive hydrostatic pressure is present proximate the taper region of the base valve member and, thereby, the plurality of linear interstices, the plurality of linear interstices being further configured and adapted to transition from the unrestricted fluid flow configuration to the restricted fluid flow configuration, wherein the plurality of linear interstices restricts retrograde blood flow into the base valve member and into and through the cardiovascular vessel, when the base valve member transitions from the expanded configuration to the contracted configuration.

In some embodiments of the invention, the base valve member comprises an ECM composition comprising ECM derived from a mammalian tissue source.

In some embodiments of the invention, the base valve member comprises crosslinked pericardium tissue, the crosslinked pericardium tissue comprising an elastic phase slope (E) in the range of 0.3 MPa to 0.5 MPa.

In some embodiments of the invention, the base valve member comprises a polymeric composition comprising at least one biocompatible polymer.

As indicated above, the prosthetic venous valves of the invention described above provide numerous advantages over prior art prosthetic venous valves. Among the advantages are the following:

The provision of prosthetic venous valves that provide optimum blood flow modulation and characteristics.

The provision of prosthetic venous valves that comprise an optimal sheet structure, including (i) increased flow modulation means (i.e., leaflet) coaptation surface area compared to conventional prosthetic valve structures, which minimizes blood flow turbulence within the valve body, and (ii) an increased flow modulation means coaptation length compared to conventional prosthetic valve structures, which, when engaged in a venous vessel, decreases the likelihood of retrograde blood flow into the valves, and, hence, into and through venous vessels.

The provision of prosthetic venous valves that are fully functional without a support structure, e.g., stent frame.

The provision of prosthetic venous valves that comprise a plurality of "independent" flow modulation means, whereby, if one flow modulation means is defective or fails, valve function is minimally disrupted, if at all.

The provision of prosthetic venous valves that enhance the velocity of antegrade blood flow into and through the valves and, hence, into and through venous vessels when engaged thereto.

The provision of prosthetic venous valves that reduce venous vessel wall shear stress (WSS), when engaged in the vessel and an antegrade blood flow is directed into the vessel.

The provision of prosthetic venous valves that can be disposed over native venous valves without resection of the native leaflets or fixing the leaflets in an open configuration.

The provision of prosthetic venous valves with minimal in vivo calcification and cytotoxicity.

The provision of prosthetic venous valves that are adapted to deliver biologically active agents, such as growth factors, and pharmacological agents, such as anti-inflammatories, to cardiovascular vessels and associated tissue, when disposed proximate thereto.

The provision of methods for replacing diseased or defective native venous valves with improved prosthetic venous valves.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A prosthetic venous valve for modulating fluid flow through a cardiovascular vessel, comprising:

a base valve member comprising crosslinked mammalian collagenous tissue, said crosslinked mammalian collagenous tissue comprising crosslinked pericardium tissue, said crosslinked pericardium tissue comprising an elastic phase slope (E) in the range of 0.3 MPa to 0.5 MPa, said base valve member comprising a taper region, an internal region, an exterior region, an open proximal valve member end and a closed distal valve member end, said open proximal valve member end being configured and adapted to engage said cardiovascular vessel, receive antegrade blood flow therein and direct said antegrade blood flow into said internal region of said base valve member, said open proximal valve member end defining an open valve inlet end comprising a first open area, said base valve member further comprising a plurality of linear interstices disposed in said taper region of said base valve member between said open proximal valve member end and said closed distal valve member end, said base valve member, when engaged to said cardiovascular vessel, being configured and adapted to expand and transition from a contracted configuration to an expanded configuration when said open proximal valve member end of said base valve member directs said antegrade blood flow into said internal region of said base valve member, and first antegrade blood of said antegrade blood flow comprises a first positive fluid pressure ≥3 mm Hg, whereby a negative hydrostatic pressure gradient is present proximate said taper region of said base valve member, said plurality of linear interstices being configured and adapted to transition from a restricted fluid flow configuration to an unrestricted fluid flow configuration, wherein said plurality of linear interstices allows said antegrade blood flow to be transmitted through and out of said base valve member and, thereby, into and through said cardiovascular vessel, when said base valve member expands and transitions from said contracted configuration to said expanded configuration, said base valve member being further configured and adapted to transition from said expanded configuration to said contracted configuration when a positive hydrostatic pressure is present proximate said taper region of said base valve member, said plurality of linear interstices being further configured and adapted to transition from said unrestricted fluid flow configuration to said restricted fluid flow configuration, wherein said plurality of linear interstices restricts retrograde blood flow into said base valve member and, thereby, into and through said cardiovascular vessel, when said base valve member transitions from said expanded configuration to said contracted configuration.

2. The prosthetic venous valve of claim 1, wherein said crosslinked pericardium tissue comprises a tensile strength in the range of 9 MPa to 12 MPa.

3. The prosthetic venous valve of claim 1, wherein said plurality of linear interstices in said unrestricted fluid flow configuration define a fluid outlet area of said base valve member, said fluid outlet area of said base valve member being at least two times greater than said first open area of said open valve inlet end.

4. The prosthetic venous valve of claim 1, wherein said crosslinked pericardium tissue comprises crosslinked bovine pericardium tissue.

5. The prosthetic venous valve of claim 1, wherein said crosslinked pericardium tissue comprises a pharmacological agent.

6. The prosthetic venous valve of claim 5, wherein said pharmacological agent comprises a pharmacological agent selected from the group consisting of desoximetasone, sirolimus, cyclosporine and prednisolone.

7. The prosthetic venous valve of claim 5, wherein said pharmacological agent comprises a HMG-CoA reductase inhibitor selected from the group consisting of atorvastatin, cerivastatin, fluvastatin and lovastatin.

8. The prosthetic venous valve of claim 1, wherein said crosslinked pericardium tissue is derived from pericardium tissue devoid of xenogeneic antigens.

9. A prosthetic venous valve for modulating fluid flow through a cardiovascular vessel, comprising:

a base valve member comprising crosslinked mammalian collagenous tissue, said crosslinked mammalian collagenous tissue comprising crosslinked pericardium tissue, said crosslinked pericardium tissue comprising an elastic phase slope (E) in the range of 0.3 MPa to 0.5 MPa, said base valve member comprising a taper region, an internal region, an exterior region, an open proximal valve member end and a closed distal valve member end, said open proximal valve member end being configured and adapted to engage said cardiovascular vessel, receive antegrade blood flow therein and direct said antegrade blood flow into said internal region of said base valve member, said open proximal valve member end defining an open valve inlet end comprising a first open area, said base valve member further comprising a plurality of linear interstices disposed in said taper region of said base valve member between said open proximal valve member end and said closed distal valve member end, said base valve member, when engaged to said cardiovascular vessel, being configured and adapted to expand and transition from a contracted configuration to an expanded configuration when said open proximal valve member end of said base valve member directs said antegrade blood flow into said internal region of said base valve member, and first antegrade blood of said antegrade blood flow comprises a first positive fluid pressure ≥3 mm Hg, whereby a first positive pressure differential between first internal valvular pressure and first external valvular pressure is generated proximate said taper region of said base valve member, said plurality of linear interstices being configured and adapted to transition from a restricted fluid flow configuration to an unrestricted fluid flow configuration, wherein said plurality of linear interstices allows said antegrade blood flow to be transmitted through and out of said base valve member and, thereby, into and through said cardiovascular vessel, when said base valve member expands and transitions from said contracted configuration to said expanded configuration, said base valve member being further configured and adapted to transition from said expanded configuration to said contracted configuration when said first positive pressure differential transitions to a second pressure differential between second internal valvular pressure and second external valvular pressure, said second pressure differential being lower than said first positive pressure differential, said plurality of linear interstices being further configured and adapted to transition from said unrestricted fluid flow configuration to said restricted fluid flow configuration, wherein said plurality of linear interstices restricts retrograde blood flow into said base valve member and, thereby, into and through said cardiovascular vessel, when said base valve member transitions from said expanded configuration to said contracted configuration.

10. The prosthetic venous valve of claim 9, wherein said crosslinked pericardium tissue comprises a tensile strength in the range of 9 MPa to 12 MPa.

11. The prosthetic venous valve of claim 9, wherein said plurality of linear interstices in said unrestricted fluid flow configuration define a fluid outlet area of said base valve member, said fluid outlet area of said base valve member being at least two times greater than said first open area of said open valve inlet end.

12. The prosthetic venous valve of claim 9, wherein said crosslinked pericardium tissue comprises crosslinked bovine pericardium tissue.

13. The prosthetic venous valve of claim 9, wherein said crosslinked pericardium tissue comprises a pharmacological agent.

14. The prosthetic venous valve of claim 13, wherein said pharmacological agent comprises a pharmacological agent selected from the group consisting of desoximetasone, sirolimus, cyclosporine and prednisolone.

15. The prosthetic venous valve of claim 13, wherein said pharmacological agent comprises a HMG-CoA reductase inhibitor selected from the group consisting of atorvastatin, cerivastatin, fluvastatin and lovastatin.

16. The prosthetic venous valve of claim 9, wherein said crosslinked pericardium tissue is derived from pericardium tissue devoid of xenogeneic antigens.

* * * * *